United States Patent
Orita et al.

(10) Patent No.: US 8,647,649 B2
(45) Date of Patent: Feb. 11, 2014

(54) EMULSIFIED COMPOSITION

(75) Inventors: Masanori Orita, Sumida-ku (JP); Tomokazu Yoshida, Sumida-ku (JP); Chihiro Ueyama, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/382,298

(22) PCT Filed: Jul. 6, 2010

(86) PCT No.: PCT/JP2010/004414
§ 371 (c)(1), (2), (4) Date: Jan. 5, 2012

(87) PCT Pub. No.: WO2011/004589
PCT Pub. Date: Jan. 13, 2011

(65) Prior Publication Data
US 2012/0108661 A1 May 3, 2012

(30) Foreign Application Priority Data

Jul. 6, 2009 (JP) ................. 2009-159737
Jul. 6, 2009 (JP) ................. 2009-159738

(51) Int. Cl.
*A61K 8/00* (2006.01)

(52) U.S. Cl.
USPC .......................................... 424/401; 424/70

(58) Field of Classification Search
USPC .................................. 424/401, 70
See application file for complete search history.

(56) References Cited

U.S. PATENT DOCUMENTS

| 2003/0175232 A1* | 9/2003 | Elliott et al. ............. 424/70.14 |
| 2004/0248294 A1 | 12/2004 | Chopart et al. |
| 2005/0152865 A1 | 7/2005 | Yamamoto et al. |
| 2007/0148771 A1 | 6/2007 | Chopart et al. |
| 2010/0184733 A1 | 7/2010 | Korevaar et al. |

FOREIGN PATENT DOCUMENTS

| JP | 2003-171229 | | 6/2003 | |
| JP | 2003-171269 | | 6/2003 | |
| JP | 2007-022997 | * | 1/2007 | ....... A61K 8/00 |
| JP | 2007 22997 | | 2/2007 | |
| JP | 2007-022997 A | * | 2/2007 | |
| JP | 2007-246538 | | 9/2007 | |
| JP | 2008 120731 | | 5/2008 | |
| JP | 2008 127341 | | 6/2008 | |
| JP | 2008-297301 | | 12/2008 | |
| JP | 2008-308462 | | 12/2008 | |
| JP | 2010-505886 | | 2/2010 | |

OTHER PUBLICATIONS

International Search Report Issued Sep. 21, 2010 in PCT/JP10/04414 Filed Jul. 6, 2010.
Combined Chinese Office Action and Search Report issued Feb. 16, 2013 in Chinese Patent Application No. 201080030512.2 (with partial English-language translation and English Translation of Categories of Cited Documents).

* cited by examiner

*Primary Examiner* — Janet Epps-Smith
*Assistant Examiner* — Yanzhi Zhang
(74) *Attorney, Agent, or Firm* — Oblon, Spivak, McClelland, Maier & Neustadt, L.L.P.

(57) ABSTRACT

The emulsion composition of the present invention contains
(A) 0.001 to 10 wt. % of an organic compound having two or more hydroxyl groups, an inorganic value of 220 to 450, and an organic value of 300 to 1,000;
(B) 0.001 to 10 wt. % of an organic compound having one hydroxyl group, an inorganic value of 100 to 200, and an organic value of 280 to 700;
(C) 0.001 to 10 wt. % of a compound represented by formula (2):
wherein $R^1$ is a C4 to C30 hydrocarbon group; Z is a methylene group, a methine group, or an oxygen atom; $X^1$, $X^2$, $X^3$ is a hydrogen atom, a hydroxyl group, or an acetoxy group; $X^4$ is a hydrogen atom, an acetyl group, or a glyceryl group; each of $R^2$ and $R^3$ a hydrogen atom, a hydroxyl group, a hydroxymethyl group, or an acetoxymethyl group; $R^4$ is a C5 to C60 hydrocarbon group; and $R^5$ is a hydrogen atom or a hydrocarbon group containing 1 to 30 carbon atoms in total;
(D) 0.00012 to 10 wt. % of at least one compound selected from the group consisting of a nonionic surfactant having a polyoxyethylene group and an HLB of 10 or higher, an ionic surfactant, and a sphingosine salt;
(E) 0.003 to 15 wt. % of at least one compound selected from the group consisting of a sugar alcohol selected from the group consisting of erythritol, threitol, xylitol, and mannitol, a disaccharide, and a trisaccharide; and
(F) water.

(2)

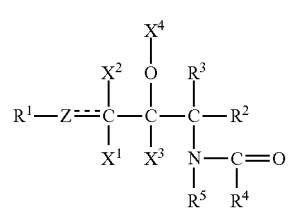

6 Claims, 1 Drawing Sheet

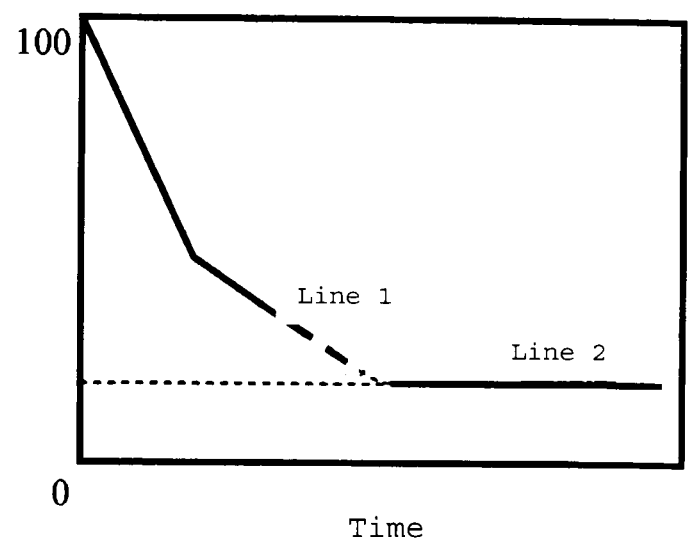

EMULSIFIED COMPOSITION

CROSS REFERENCE TO RELATED APPLICATION

This application is a 371 of PCT/2010/004414, filed on Jul. 6, 2010, and claims priority to the following Japanese Applications: JP 2009-159737, filed on Jul. 6, 2009; and JP 2009-159738, filed on Jul. 6, 2009.

FIELD OF THE INVENTION

The present invention relates to an emulsion composition which allows water to remain in the skin for a long period of time.

BACKGROUND OF THE INVENTION

α-Gel has a hydrate-type crystal structure, which is a lamellar structure. The intercellular lipid present in the horny layer (i.e., the outermost skin layer) generally has the α-gel structure, and prevents entry of outside substances into the skin as well as transepidermal water loss. Also, the intercellular lipid itself retains water, whereby the softness and smooth appearance of the skin can be maintained. In the skin, the horny layer retains water as bound water in an amount of about 33%. Studies have revealed that the intercellular lipid retains about 13% of the bound water (here, bound water is defined as water restrained by molecules forming the horny layer) (Non-Patent Document 1).

For example, Patent Document 1 discloses that an emulsion composition containing a ceramide and other ingredients forms an α-gel structure, to thereby enhance a moisturizing effect. When the skin surface is covered with such an α-gel, as covered with the intercellular lipid, the skin is expected to retain a sufficient amount of water under dry conditions, to thereby attain long-lasting moistness.

Meanwhile, low-molecular-weight compounds such as glycerin and amino acid as well as high-molecular-weight compounds such as hyaluronic acid are thought to have a high moisture retention property. However, since the water content of an aqueous solution of a single ingredient is generally limited to the bound water level, a preparation containing such an ingredient attains unsatisfactory water retention. In addition, although the aforementioned α-gel is expected to exhibit satisfactory water retention, solid fat that constitutes α-gel provides users a heavy feeling upon use. Thus, when the amount of α-gel is simply increased to enhance water retention, a good feeling upon use is impaired (e.g., sticky feeling upon use).

PRIOR ART DOCUMENTS

Non-Patent Documents

Non-Patent Document 1: Genji IMOKAWA, Oil Chemistry, 44, 10, p. 51-66(1995)

Patent Documents

Patent Document 1: JP-A-2007-22997

SUMMARY OF THE INVENTION

Problems to be Solved by the Invention

The present invention is directed to an emulsion composition which can retain bound water and free water (i.e., water retained in the interlamellar layers but not restrained by a lamellar structure ingredient) in the interlamellar layers of an α-gel lamellar structure, allowing water to be retained in the skin for a long period of time, to thereby improve skin conditions.

Means for Solving the Problems

The present inventors have found that, through a combination of an α-gel designed to have enhanced water retention with a specific sugar alcohol, disaccharide, or trisaccharide, there can be produced an emulsion composition which can enhance water retention of α-gel, allowing water to be retained in the skin for a long period of time, to thereby improve skin conditions.

The present invention provides an emulsion composition containing the following ingredients (A), (B), (C), (D), (E), and (F):

(A) 0.001 to 10 wt. % of an organic compound having two or more hydroxyl groups, an inorganic value of 220 to 450, and an organic value of 300 to 1,000;

(B) 0.001 to 10 wt. % of an organic compound having one hydroxyl group, an inorganic value of 100 to 200, and an organic value of 280 to 700;

(C) 0.001 to 10 wt. % of a compound represented by formula (2):

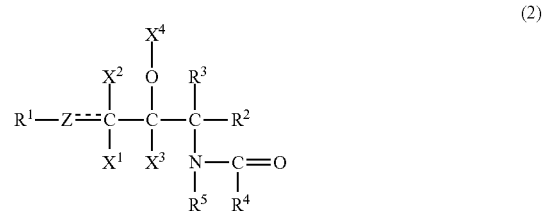

(wherein $R^1$ represents a C4 to C30 linear, branched, or cyclic, saturated or unsaturated hydrocarbon group which may be substituted by a hydroxyl group, a carbonyl group, or an amino group; Z represents a methylene group, a methine group, or an oxygen atom; each of $X^1$, $X^2$, and $X^3$ represents a hydrogen atom, a hydroxyl group, or an acetoxy group; $X^4$ represents a hydrogen atom, an acetyl group, or a glyceryl group, or forms an oxo group together with the adjacent oxygen atom (wherein when Z is a methine group, one of $X^1$ and $X^2$ is a hydrogen atom, and the other is absent, and when $X^4$ forms an oxo group, $X^3$ is absent); each of $R^2$ and $R^3$ represents a hydrogen atom, a hydroxyl group, a hydroxymethyl group, or an acetoxymethyl group; $R^4$ represents a C5 to C60 linear, branched, or cyclic, saturated or unsaturated hydrocarbon group which may be substituted by a hydroxyl group, a carbonyl group, or an amino group and which may have an ether bond, an ester bond, or an amide bond in a backbone thereof; $R^5$ represents a hydrogen atom, or a linear or branched, saturated or unsaturated hydrocarbon group optionally having a substituent selected from the group consisting of a hydroxyl group, a hydroxyalkoxy group, an alkoxy group, and an acetoxy group and containing 1 to 30 carbon atoms in total; and the broken line represents an optional unsaturated bond);

(D) 0.00012 to 10 wt. % of at least one compound selected from the group consisting of a nonionic surfactant having a polyoxyethylene group and an HLB of 10 or higher, an ionic surfactant, and a sphingosine salt;

(E) 0.003 to 15 wt. % of at least one compound selected from the group consisting of a sugar alcohol selected from the group consisting of erythritol, threitol, xylitol, and mannitol, a disaccharide, and a trisaccharide; and (F) water.

Effects of the Invention

The emulsion composition of the present invention contains, as active ingredients, ingredients (A), (B), and (C) and forms a uniform a structure having high steric regularity. Thus, the emulsion composition has enhanced water retention and allows water to remain in the skin for a long period of time, whereby the skin conditions can be improved. When the composition is applied to the skin, excellent skin permeability and long-lasting moistness can be obtained. In addition, the composition enables formation on the skin surface of a soft coating layer having a lamellar-like structure, whereby water can be retained in the interlayer space, to thereby enhance a skin protection effect.

BRIEF DESCRIPTION OF THE DRAWINGS

FIG. 1 A graph employed for measuring remaining water content in the Examples and Comparative Examples.

MODES FOR CARRYING OUT THE INVENTION

[Ingredient (A)]

Ingredient (A) employed in the present invention is an organic compound having two or more hydroxyl groups, an inorganic value of 220 to 450, and an organic value of 300 to 1,000. Preferable examples of ingredient (A) include an organic compound having an inorganic value of 220 to 340 and an organic value of 380 to 840, more preferably an organic compound having an inorganic value of 250 to 340 and organic value of 380 to 700, from the viewpoint of formability of a lamellar structure with the below-mentioned other ingredients.

In the present invention, the terms "inorganic value" and "organic value" refer to those obtained from an organic conceptual diagram (see "Prediction of Organic Compounds by a Conceptual Diagram" described by Atsushi FUJITA, *Kagaku-no-Ryouiki*, Vol. 11, No. 10 (1957) 719-725).

Examples of ingredient (A) include compounds represented by formula (1):

$$Z^1-(Y^1-R)_n \quad (1)$$

(wherein $Z^1$ represents a structure which is a glycerin residue, a sorbitan residue, a sorbitol residue, or a sucrose residue having two or more hydroxyl groups; $Y^1$ represents an ester bond or an ether bond; R represents a C14 to C22 hydrocarbon group; and n is a number of 1 or 2).

In formula (1), the C14 to C22 hydrocarbon group R is preferably a linear hydrocarbon group, such as a linear alkyl group (e.g., myristyl, palmityl, stearyl, or behenyl), a palmitoyl group, or an oleyl group.

Examples of the compound represented by formula (1) include glycerin monofatty acid ester, sorbitan monofatty acid ester, sorbitan difatty acid ester, sorbitol monofatty acid ester, sorbitol difatty acid ester, sucrose monofatty acid ester, and glycerin monoalkyl ether.

Ingredient (A) is preferably glycerin monofatty acid ester, glycerin monoalkyl ether, sorbitan monofatty acid ester, or sorbitan difatty acid ester. Among them, glyceryl monopalmitate (inorganic value 260, organic value 380), glyceryl monostearate (inorganic value 260, organic value 420), glyceryl monobehenate (inorganic value 260, organic value 500), monocetyl glyceryl ether (inorganic value 220, organic value 380), monostearyl glyceryl ether (inorganic value 220, organic value 420), sorbitan monostearate (inorganic value 445, organic value 480), and sorbitan distearate (inorganic value 340, organic value 840) are preferred. Of these, glyceryl monobehenate and monocetyl glyceryl ether are more preferred, for enhancing lamellar film formability and water retention, as mentioned hereinbelow.

Ingredient (A) employed in the present invention may be one or more species. The composition of the invention has an ingredient (A) content of 0.001 to 10 wt. %, preferably 0.05 to 7 wt. %, more preferably 0.1 to 3 wt. %, in the total composition, since water retention is enhanced.

[Ingredient (B)]

Ingredient (B) employed in the present invention is an organic compound having one hydroxyl group, an inorganic value of 100 to 200, and an organic value of 280 to 700. For ingredient (B), more preferred is an organic compound having an inorganic value of 100 to 182 and an organic value of 300 to 520, from the viewpoint of formability of a lamellar structure with ingredient (A) and the below-mentioned ingredients.

Specific examples of the organic compound include one or more compounds selected from the group consisting of a C14 to C22 higher alcohol and a sterol.

The higher alcohol is a C14 to C22 alcohol, preferably C16 to C18 alcohol. Examples of the higher alcohol include myristyl alcohol (inorganic value 100, organic value 280), cetanol (inorganic value 100, organic value 320), stearyl alcohol (inorganic value 100, organic value 360), behenyl alcohol (inorganic value 100, organic value 440), and oleyl alcohol (inorganic value 102, organic value 360).

Among them, an alcohol having a linear alkyl group is preferred, with cetanol and stearyl alcohol being more preferred.

Examples of the sterol include cholesterol (inorganic value 182, organic value 520) and phytosterol. The term "phytosterol" collectively refers to plant-derived sterols such as β-sitosterol, campesterol, stigmasterol, and brassicasterol, and no particular limitation is imposed on the ingredient composition thereof.

Ingredient (B) employed in the composition may include one or more species. The composition contains ingredient (B) in an amount of 0.001 to 10 wt. % with respect to the total composition, preferably 0.05 to 7 wt. %, more preferably 0.1 to 3 wt. %, for attaining high water-occluding property.

[Ingredient (C)]

Ingredient (C) employed in the present invention is a compound represented by formula (2).

In formula (2), $R^1$ represents a hydrogen atom or a C4 to C30 linear, branched, or cyclic, saturated or unsaturated hydrocarbon group which may be substituted by a hydroxyl group, a carbonyl group, or an amino group, and $R^1$ represents preferably a C7 to C22 linear, branched, or cyclic, saturated or unsaturated hydrocarbon group which may be substituted by a hydroxyl group.

Z represents a methylene group, a methine group, or an oxygen atom.

Each of $X^1$, $X^2$, and $X^3$ represents a hydrogen atom, a hydroxyl group, or an acetoxy group. In a preferred embodiment, all of $X^1$, $X^2$, and $X^3$ are not a hydroxyl group or one of $X^1$, $X^2$, and $X^3$ is a hydroxyl group, and each of the remaining groups is a hydrogen atom. When Z is a methine group, one of $X^1$ and $X^2$ is a hydrogen atom, and the other is absent. $X^4$ is preferably a hydrogen atom or a glyceryl group.

Each of $R^2$ and $R^3$ represents a hydrogen atom, a hydroxyl group, a hydroxymethyl group, or an acetoxymethyl group. $R^2$ is preferably a hydrogen atom or a hydroxymethyl group, and $R^3$ is preferably a hydrogen atom.

$R^4$ represents a C5 to C60 linear, branched, or cyclic, saturated or unsaturated hydrocarbon group which may be substituted by a hydroxyl group, a carboxyl group, or an amino group and which may have an ether bond, an ester bond, or an amide bond in a backbone thereof. $R^4$ is preferably, for example, a C5 to C35 linear, branched, or cyclic, saturated or unsaturated hydrocarbon group optionally substituted by a hydroxyl group or an amino group, or a group formed by bonding a C8 to C22 linear, branched, or cyclic, saturated or unsaturated fatty acid optionally having a hydroxyl group to the ω-position of the above hydrocarbon group via an ester bond or an amide bond. The fatty acid bonded to the hydrocarbon group is preferably isostearic acid, 12-hydroxystearic acid, or linoleic acid.

$R^5$ represents a hydrogen atom, or a linear or branched, saturated or unsaturated hydrocarbon group optionally having a substituent selected from the group consisting of a hydroxyl group, a hydroxyalkoxy group, an alkoxy group, and an acetoxy group and containing 1 to 30 carbon atoms in total. When $R^1$ is a hydrogen atom and Z is an oxygen atom, $R^5$ is a hydrocarbon group containing 10 to 30 carbon atoms in total. When $R^1$ is a hydrocarbon group, $R^5$ is a hydrocarbon group containing 1 to 8 carbon atoms in total. Among them, preferred are a hydrogen atom and a hydrocarbon group containing 1 to 8 carbon atoms in total which group may be substituted by 1 to 3 substituents selected from the group consisting of a hydroxyl group, a hydroxyalkoxy group, and an alkoxy group. The hydroxyalkoxy group and the alkoxy group preferably have 1 to 7 carbon atoms.

The compound represented by formula (2) is preferably a ceramide represented by the following formula (3) or (4).

(I) The compound represented by formula (3) may be a naturally occurring ceramide or a synthetic product having the same structure.

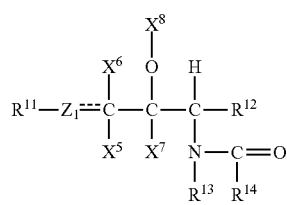

(3)

(wherein $R^{11}$ represents a C7 to C19 linear, branched or cyclic, saturated or unsaturated hydrocarbon group which may be substituted by a hydroxyl group; $Z_1$ represents a methylene group or a methine group; each of $X^5$, $X^6$, and $X^7$ represents a hydrogen atom, a hydroxyl group, or an acetoxy group; $X^8$ represents a hydrogen atom, or forms an oxo group together with the adjacent oxygen atom (wherein when $Z_1$ is a methine group, one of $X^5$ and $X^6$ is a hydrogen atom, and the other is absent, and when $X^8$ forms an oxo group, $X^7$ is absent); $R^{12}$ represents a hydroxymethyl group or an acetoxymethyl group; $R^{13}$ represents a hydrogen atom or a C1 to C4 alkyl group; $R^{14}$ represents a C5 to C30 linear, branched or cyclic, saturated or unsaturated hydrocarbon group which may be substituted by a hydroxyl group, or such an alkyl group to which a C8 to C22 linear or branched, saturated or unsaturated fatty acid which may be substituted by a hydroxyl group is bonded at the ω-end via ester bonding; and the broken line represents an optional unsaturated bond).

In a preferred compound, $R^{11}$ is a C7 to C19 (more preferably C13 to C15) linear alkyl group; $R^{14}$ is a C9 to C27 linear alkyl group which may be substituted by a hydroxyl group, or a C9 to C27 linear alkyl group to which linoleic acid is bonded via ester bonding. Preferably, $X^8$ is a hydrogen atom or forms an oxo group together with an oxygen atom. $R^{14}$ is preferably tricosyl, 1-hydroxypentadecyl, 1-hydroxytricosyl, heptadecyl, 1-hydroxyundecyl, or nonacosyl to which linoleic acid is bonded at the ω-position via ester bonding.

Specific examples of the natural-type ceramide include sphingosine, dihydrosphingosine, phytosphingosine, and amidated sphingadienine (Ceramide Types 1 to 7) (see, for example, pig-origin and human-origin ceramides shown in FIG. 2 in J. Lipid Res., 24: 759 (1983) and FIG. 4 in J. Lipid. Res., 35: 2069 (1994)).

N-alkyl forms of these ceramides are also included (e.g., N-methyl form).

Regarding these ceramides, either a natural-type optically active form (D(−) form) or a non-natural-type optically active form (L(+) form) may be used. Furthermore, a mixture of a natural-type form and a non-natural-type form may also be used. The relative configuration of the aforementioned compound may be ones of natural-type, of non-natural-type, or of mixed type. Further, preferred are compounds: CERAMIDE 1, CERAMIDE 2, CERAMIDE 3, CERAMIDE 5, CERAMIDE 611, (INCI, 8th Edition), and those represented by the following formulas.

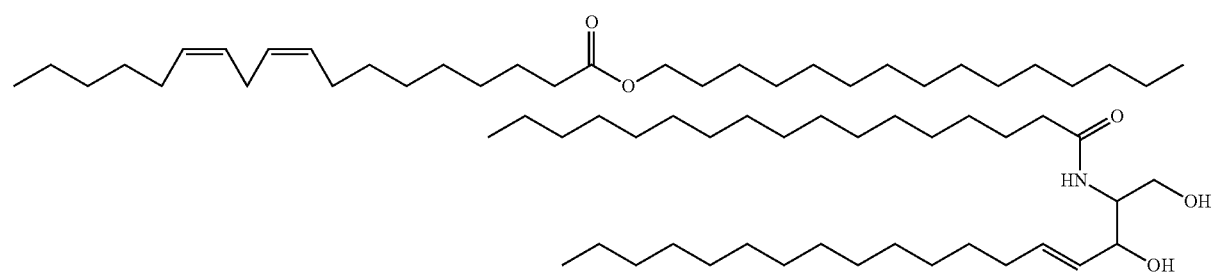

-continued
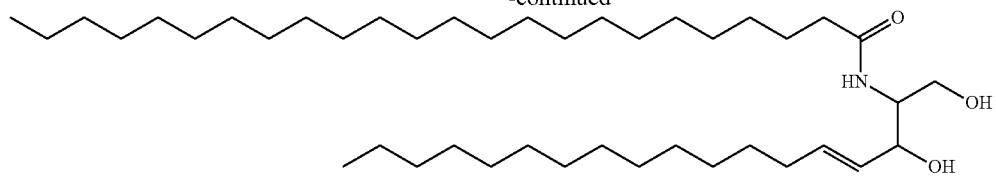
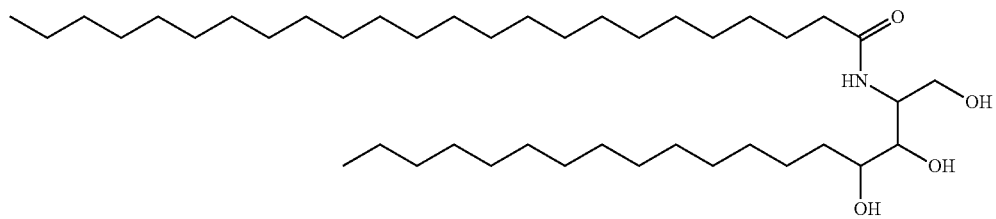
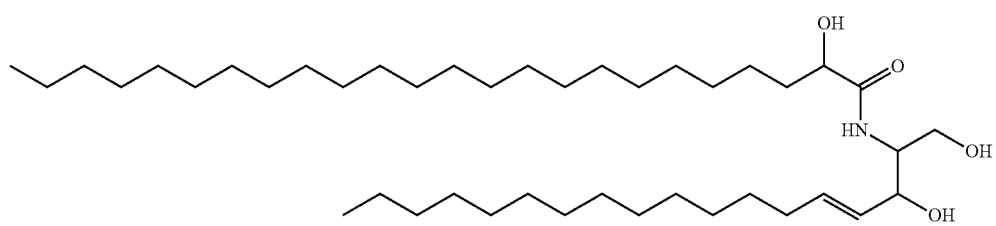
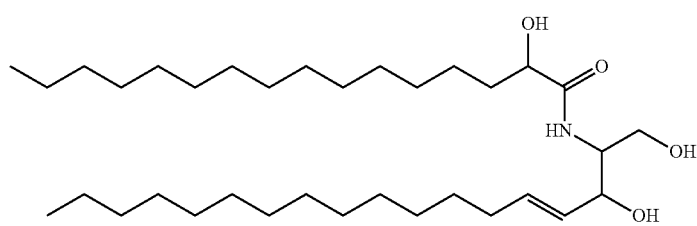
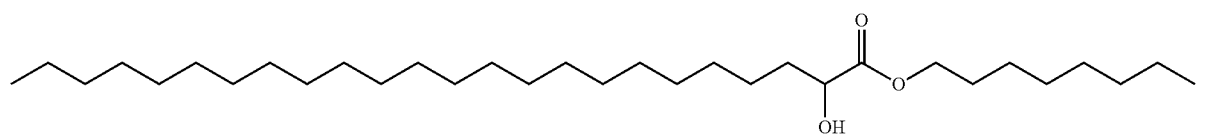
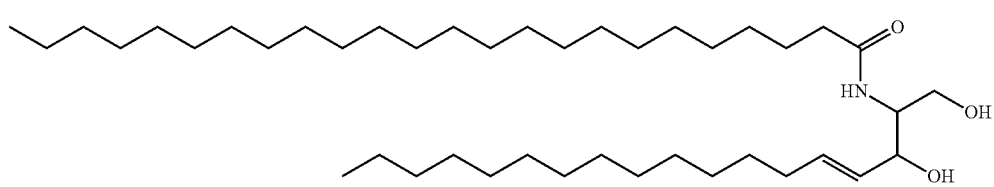
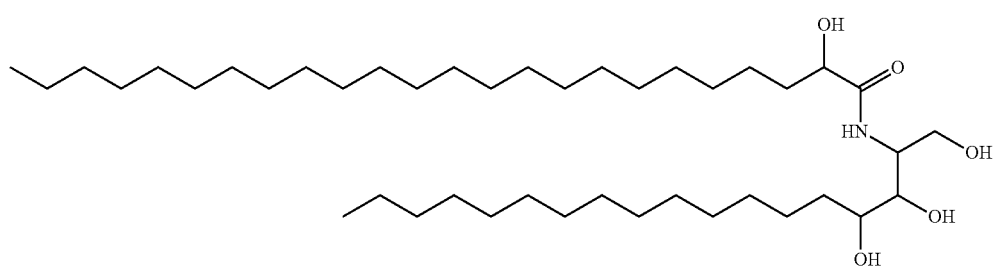

These ceramides may be either compounds extracted from natural ceramides or synthesized ones thereof. Commercially available ones can also be used.

Examples of such the commercially available natural type ceramides include Ceramide I, Ceramide III, Ceramide IIIA, Ceramide IIIB, Ceramide IIIC, and Ceramide VI (COSMOFERM); Ceramide TIC-001 (Takasago International Corporation); CERAMIDE II (Quest International); DS-Ceramide VI, DS-CLA-Phytoceramide, C6-Phytoceramide, and DS-ceramide Y3S (DOOSAN); and CERAMIDE 2 (Sederma).

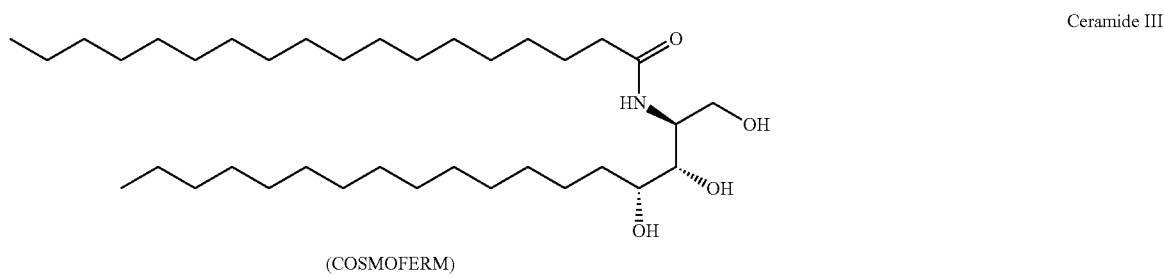

Ceramide III
(COSMOFERM)

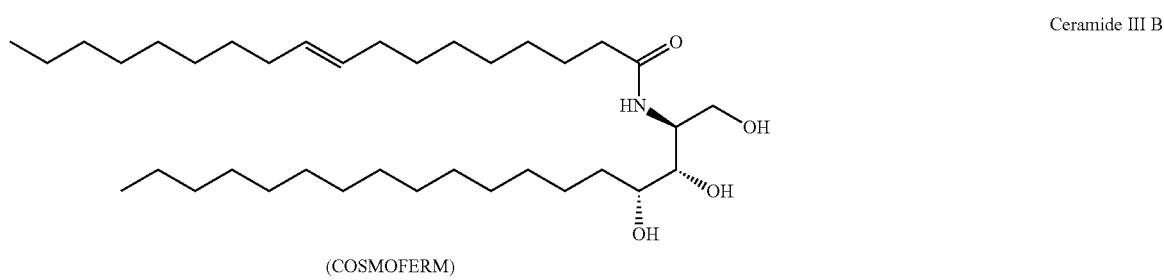

Ceramide III B
(COSMOFERM)

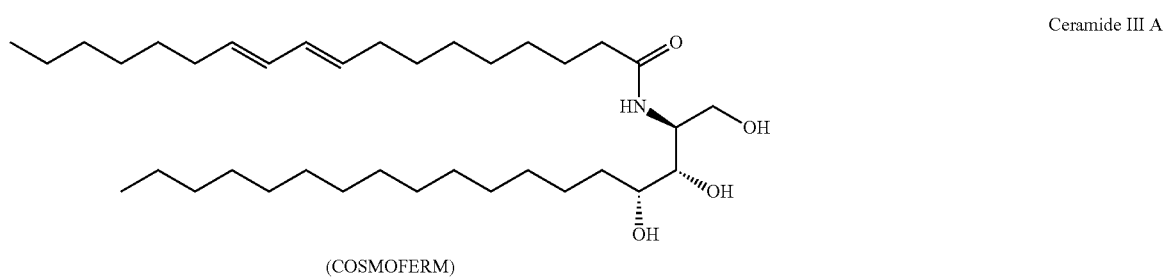

Ceramide III A
(COSMOFERM)

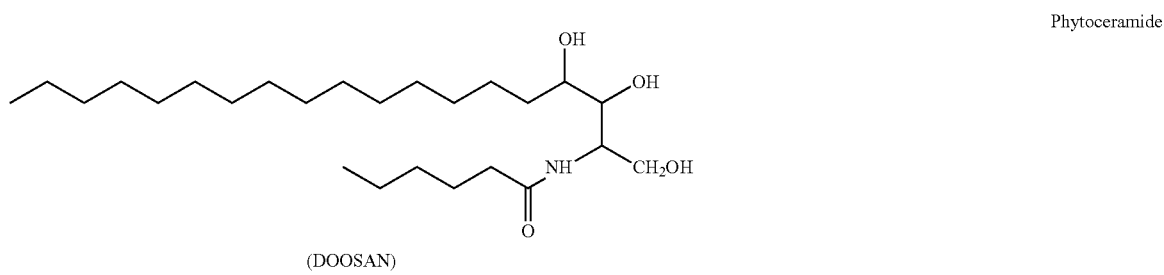

Phytoceramide
(DOOSAN)

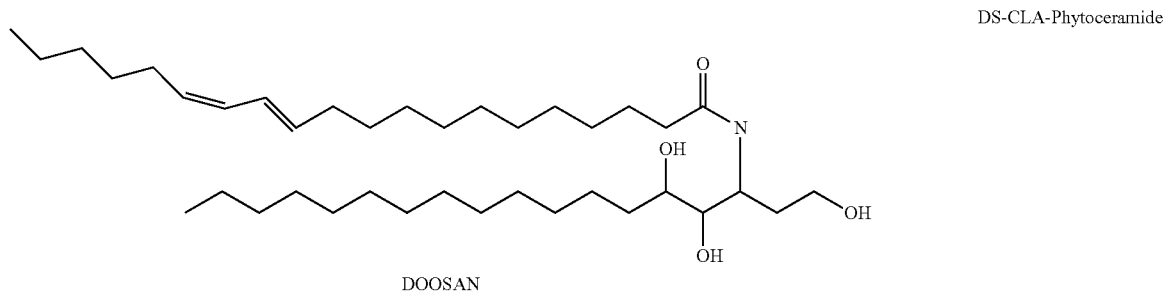

DS-CLA-Phytoceramide
DOOSAN

-continued

DS-Ceramide VI

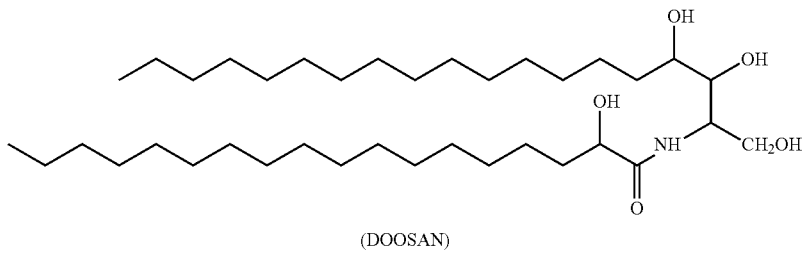

(DOOSAN)

Ceramide IV

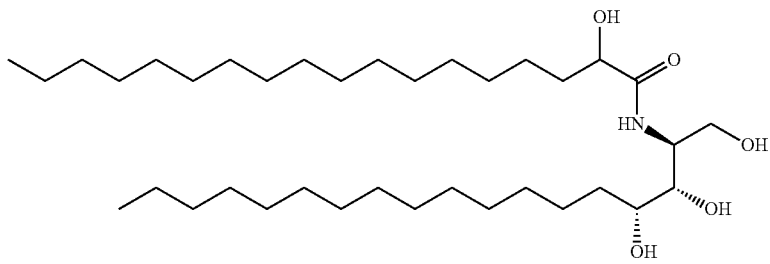

(COSMOFERM)

Ceramide I

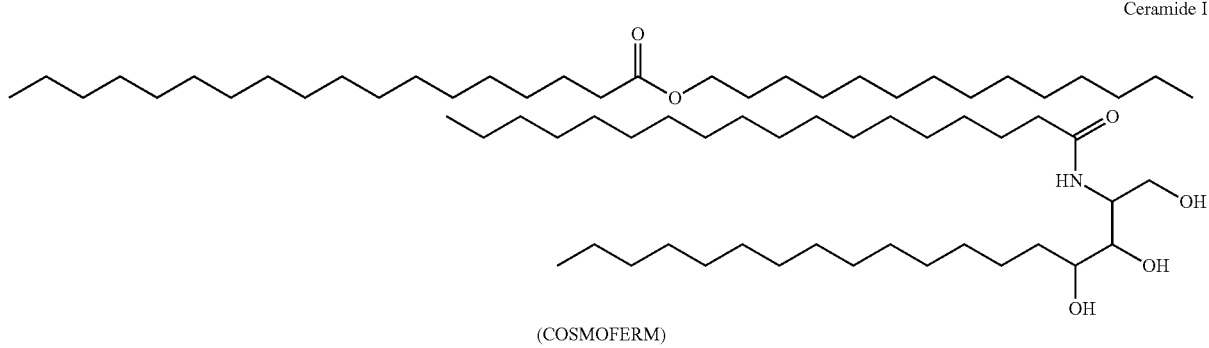

(COSMOFERM)

(II): Pseudo-ceramide represented by formula (4):

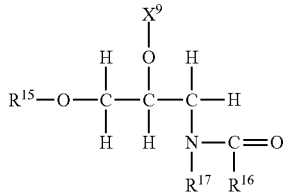

(4)

(wherein $R^{15}$ represents a hydrogen atom or a C10 to C22 linear, branched, or cyclic, saturated or unsaturated hydrocarbon group which may be substituted by a hydroxyl group; $X^9$ represents a hydrogen atom, an acetyl group, or a glyceryl group; $R^{16}$ represents a C5 to C22 linear, branched, or cyclic, saturated or unsaturated hydrocarbon group which may be substituted by a hydroxyl group or an amino group, or such a hydrocarbon group to which a C8 to C22 linear or branched, saturated or unsaturated fatty acid which may be substituted by a hydroxyl group is bonded at the ω-end via ester bonding; and $R^{17}$ represents a hydrogen atom or an alkyl group optionally having a substituent selected from the group consisting of a hydroxyl group, a hydroxyalkoxy group, an alkoxy group, and an acetoxy group and containing 1 to 30 carbon atoms in total).

$R^{16}$ is preferably nonyl, tridecyl, pentadecyl, undecyl to which linoleic acid is bonded at the ω-position thereof via ester bonding, pentadecyl to which linoleic acid is bonded at the ω-position thereof via ester bonding, pentadecyl to which 12-hydroxystearic acid is bonded at the ω-position thereof via ester bonding, or undecyl to which methyl-branched isostearic acid is bonded at the ω-position thereof via amide bonding.

When $R^{15}$ is a hydrogen atom, $R^{17}$ is an alkyl group optionally substituted by a hydroxyl group, a hydroxyalkoxy group, an alkoxy group, or an acetoxy group and containing 10 to 30 (preferably 12 to 20) carbon atoms in total. When $R^{15}$ is a C10 to C22 linear, branched, or cyclic, saturated or unsaturated hydrocarbon group which may be substituted by a hydroxyl group, $R^{17}$ is preferably a hydrogen atom or an alkyl group optionally substituted by a hydroxyl group, a hydroxyalkoxy group, an alkoxy group, or an acetoxy group and containing 1 to 8 carbon atoms in total. The hydroxyalkoxy or alkoxy group in $R^{17}$ preferably contains 1 to 7 carbon atoms.

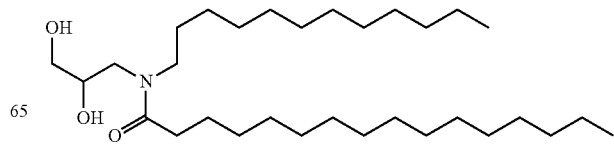

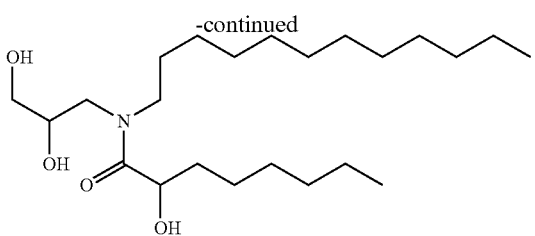

Preferred pseudo-ceramides represented by formula (4) are the case where $R^{15}$ is hexadecyl, $X^9$ is a hydrogen atom, $R^{16}$ is pentadecyl, and $R^{17}$ is hydroxyethyl; the case where $R^{15}$ is hexadecyl, $X^9$ is a hydrogen atom, $R^{16}$ is nonyl, and $R^{17}$ is hydroxyethyl; and the case where $R^{15}$ is hexadecyl, $X^9$ is glyceryl, $R^{16}$ is tridecyl, and $R^{17}$ is 3-methoxypropyl. More preferred pseudo-ceramide represented by formula (4) is the case where $R^{15}$ is hexadecyl, $X^9$ is a hydrogen atom, $R^{16}$ is pentadecyl, and $R^{17}$ is hydroxyethyl (i.e., N-(hexadecyloxyhydroxypropyl)-N-hydroxyethylhexadecanamide).

Of these, polyoxyethylene hydrogenated castor oil and polyoxyethylene sorbitan monostearate are preferred.

Among the compounds serving as ingredient (D), the ionic surfactant is an anionic surfactant, a cationic surfactant, or an ampholytic surfactant.

Examples of the anionic surfactant include C12 to C24 fatty acid salts such as sodium laurate, potassium palmitate, and arginine stearate; alkyl sulfate ester salts such as sodium lauryl sulfate and potassium lauryl sulfate; alkyl ether sulfate ester salts such as polyoxyethylene lauryl sulfate triethanolamine salt; N-acylsarcosine salts such as lauroyl sarcosine sodium salt; fatty acid amide sulfonate salts such as sodium methyl stearoyl taurate(N-stearoyl-N-methyltaurine sodium salt) and sodium methyl myristoyl taurate(N-myristoyl-N-methyltaurine sodium salt); alkyl phosphate salts such as sodium monostearyl phosphate; polyoxyethylene alkyl ether phosphate salts such as sodium polyoxyethylene oleyl ether phosphate and sodium polyoxyethylene stearyl ether phosphate; long-chain sulfosuccinate salts such as sodium di-2-ethylhexylsulfosuccinate; and long-chain N-acylglutamate

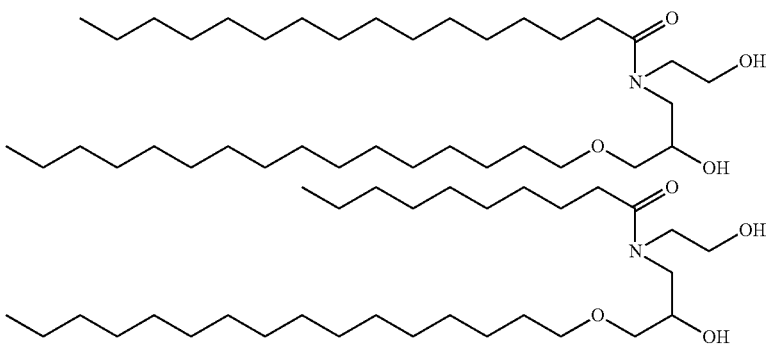

One or more compounds serving as ingredient (C) may be used. The total content of ingredient (C) is 0.001 to 10 wt. %, preferably 0.05 to 7 wt. %, more preferably 0.1 to 5 wt. %, in the total composition, for attaining sufficient skin permeation of ingredient (C).

In the present invention, the weight ratio of ingredients (A), (B), and (C) preferably have the following relationship: ((A)+(B))/((A)+(B)+(C)) (by weight) of 0.15 or more, more preferably 0.35 to 0.8, from the viewpoint of enhancing storage stability of α-gel.

The weight ratio of ingredients (A) and (B) preferably have the following relationship: (A)/((A)+(B)) (by weight) of 0.1 or more, more preferably 0.25 to 0.75, since stable α-gel structure is formed, to thereby enhance water retention.

[Ingredient (D)]

The ingredient (D) employed in the present invention is at least one compound selected from the group consisting of a nonionic surfactant having a polyoxyethylene group and an HLB of 10 or more, an ionic surfactant, and a sphingosine salt.

Among the compounds serving as ingredient (D), the nonionic surfactant is a hydrophilic compound having a polyoxyethylene group and an HLB of 10 or more, preferably an HLB of 12.5 to 15.5. Examples of the non-ionic compound include polyoxyethylene hydrogenated castor oil, polyoxyethylene sorbitan fatty acid ester, alkylpolyoxyethylene glyceryl, and polyoxyethylene alkyl ether.

salts such as monosodium N-lauroylglutamate, sodium N-stearoyl-L-glutamate, arginine N-stearoyl-L-glutamate, sodium N-stearoylglutamate, and sodium N-myristoyl-L-glutamate.

Among them, C12 to C24 fatty acid salts, fatty acid amidesulfonate salts, polyoxyethylene alkyl ether phosphate salts, and long-chain N-acylglutamate salts are preferred, with sodium methyl stearoyl taurate(N-stearoyl-N-methyltaurine sodium salt), arginine N-stearoyl-L-glutamate, and sodium polyoxyethylene stearyl ether phosphate being more preferred.

The cationic surfactant is preferably a quaternary ammonium salt. Examples include alkyltrimethylammonium salts such as stearyl trimethylammonium chloride and lauryl trimethylammonium chloride; dialkyldimethylammonium salts; trialkylmethylammonium salts; and alkylamine salts.

Examples of the ampholytic surfactant include alkyldimethylamine oxide, alkylcarboxybetaine, alkylsulfobetaine, amideamino acid salts, and alkylamidepropylbetaine. Of these, alkylamidepropylbetaine is preferred.

Among the compounds serving as ingredient (D) employed in the present invention, the sphingosine salt is formed of a sphingosine and an acidic substance. Examples of the sphingosine include those represented by formula (5):

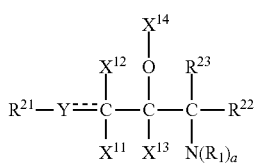

(wherein $R^{21}$ represents a C4 to C30 linear, branched, or cyclic, saturated or unsaturated hydrocarbon group which may be substituted by a hydroxyl group, a carbonyl group, or an amino group; Y represents a methylene group, a methine group, or an oxygen atom; each of $X^{11}$, $X^{12}$, and $X^{13}$ represents a hydrogen atom, a hydroxyl group, or an acetoxy group; $X^{14}$ represents a hydrogen atom, an acetyl group, or a glyceryl group, or forms an oxo group together with the adjacent oxygen atom (wherein when Y is a methine group, one of $X^{11}$ and $X^{12}$ is a hydrogen atom, and the other is absent, and when $X^{14}$ forms an oxo group, $X^{13}$ is absent); each of $R^{22}$ and $R^{23}$ represents a hydrogen atom, a hydroxyl group, a hydroxymethyl group, or an acetoxymethyl group; each of the "a" groups of $R_1$s represents a hydrogen atom, an amidino group, or a linear or branched, saturated or unsaturated hydrocarbon group optionally having a substituent selected from the group consisting of a hydroxyl group, a hydroxyalkoxy group, an alkoxy group, and an acetoxy group and containing 1 to 8 carbon atoms in total; a is a number of 2 or 3; and the broken line represents an optional unsaturated bond).

In formula (5), $R^{21}$ is C4 to C30 linear, branched, or cyclic, saturated or unsaturated hydrocarbon group which may be substituted by a hydroxyl group, a carbonyl group, or an amino group, and $R^{21}$ represents preferably a C7 to C22 linear, branched, or cyclic, saturated or unsaturated hydrocarbon group which may be substituted by a hydroxyl group. Also preferred are a C10 to C20 linear or branched alkyl group and a C10 to C20 linear or branched alkyl group having a hydroxyl group on the carbon atom bonding to Y in formula (5), wherein when the alkyl is of a branched type, the branched alkyl is preferably, for example, a methyl branching fashion alkyl. Specific examples of preferred alkyl groups include tridecyl, tetradecyl, pentadecyl, hexadecyl, 1-hydroxytridecyl, 1-hydroxypentadecyl, isohexadecyl, and isostearyl.

Y represents a methylene group ($CH_2$), a methine group (CH), or an oxygen atom.

Each of $X^{11}$, $X^{12}$, and $X^{13}$ is a hydrogen atom, a hydroxyl group, or an acetoxy group. $X^{14}$ is a hydrogen atom, an acetyl group, or a glyceryl group, or a substituent which forms an oxo group together with the adjacent oxygen atom. In a preferred embodiment, all of $X^{11}$, $X^{12}$, and $X^{13}$ are not a hydroxyl group, or one of $X^{11}$, $X^{12}$, and $X^{13}$ is a hydroxyl group, and the remaining groups are a hydrogen atom, and $X^{14}$ is a hydrogen atom. When Y is a methine group, one of $X^{11}$ and $X^{12}$ is a hydrogen atom, and the other is absent. When $X^{14}$ forms an oxo group, $X^{13}$ is absent.

Each of $R^{22}$ and $R^{23}$ is a hydrogen atom, a hydroxyl group, a hydroxymethyl group, or an acetoxymethyl group. $R^{23}$ is preferably a hydrogen atom.

The symbol "a" is a number of 2 or 3. When a is 2, $R_1$ correspond to $R^{24}$ and $R^{25}$, and when a is 3, $R_1$ correspond to $R^{24}$, $R^{25}$, and $R^{26}$.

Each of $R^{24}$, $R^{25}$, and $R^{26}$ represents a hydrogen atom, an amidino group, or a linear or branched, saturated or unsaturated hydrocarbon group optionally having a substituent selected from the group consisting of a hydroxyl group, a hydroxyalkoxy group, an alkoxy group, and an acetoxy group and containing 1 to 8 carbon atoms in total. The hydroxyalkoxy group which can serve as a substituent of the hydrocarbon group is preferably a C1 to C7 linear or branched hydroxyalkoxy group. The alkoxy group is preferably a C1 to C7 linear or branched alkoxy group. Examples of $R^{24}$, $R^{25}$, and $R^{26}$ include hydrocarbon groups each having 1 to 8 carbon atoms in total and being substituted by 1 to 6 substituents. Examples of the substituents include a hydrogen atom; linear or branched alkyl groups such as methyl, ethyl, propyl, 2-ethylhexyl, and isopropyl; alkenyl groups such as vinyl and allyl; an amidino group; hydroxyl groups such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl; hydroxyalkoxy groups, and alkoxy groups.

Among them, more preferred are a hydrogen atom and alkyl groups each being substituted by 1 to 3 groups selected from the group consisting of methyl, hydroxyl groups such as 2-hydroxyethyl, 1,1-dimethyl-2-hydroxyethyl, 1,1-bis(hydroxymethyl)ethyl, and 2-(2-hydroxyethoxy)ethyl, and hydroxyalkoxy groups.

The sphingosine represented by formula (5) is preferably a naturally occurring sphingosine represented by formula (6), a synthetic product having the same structure, or a derivative of any of these (hereinafter referred to as natural-type sphingosine); or a pseudo-sphingosine represented by formula (7) having a sphingosine structure (hereinafter referred to as pseudo-sphingosine).

(I) Natural-type sphingosine represented by formula (6):

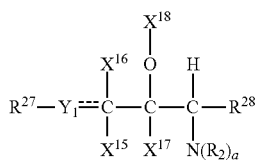

(wherein $R^{27}$ represents a C7 to C19 linear, branched, or cyclic, saturated or unsaturated hydrocarbon group which may be substituted by a hydroxyl group; $Y_1$ represents a methylene group or a methine group; each of $X^{15}$, $X^{16}$, and $X^{17}$ represents a hydrogen atom, a hydroxyl group, or an acetoxy group; $X^{18}$ represents a hydrogen atom or forms an oxo group together with the adjacent oxygen atom (wherein when $Y_1$ is a methine group, one of $X^{15}$ and $X^{16}$ is a hydrogen atom, and the other is absent, and when $X^{18}$ forms an oxo group, $X^{17}$ is absent); $R^{28}$ represents a hydroxymethyl group or an acetoxymethyl group; each of the "a" groups of $R_2$s represents a hydrogen atom, an amidino group, or a linear or branched, saturated or unsaturated hydrocarbon group optionally having a substituent selected from the group consisting of a hydroxyl group, a hydroxyalkoxy group, an alkoxy group, and an acetoxy group and containing 1 to 4 carbon atoms in total; a is a number of 2 or 3; and the broken line represents an optional unsaturated bond).

$R^{27}$ is preferably a C7 to C19 linear, branched, or cyclic, saturated or unsaturated hydrocarbon group, more preferably a C13 to C15 linear, saturated or unsaturated hydrocarbon group. The number "a" is preferably 2. Each of $R_2$s is preferably a hydrogen atom or a C1 to C4 linear or branched alkyl group.

Specific examples of the natural-type sphingosine represented by formula (6) include sphingosine, dihydrosphingosine, phytosphingosine, sphingadienine, dehydrosphingosine, and dehydrophytosphingosine, and N-alkyl derivatives thereof (e.g., N-methyl derivatives).

Regarding these sphingosines, either a natural-type optically active form (D(+) form) or a non-natural-type optically active form (L(−) form) may be used. Furthermore, a mixture of a natural-type form and a non-natural-type form may also be used. The relative configuration of the aforementioned compound may be ones of natural-type, of non-natural-type, or of mixed type.

Examples of preferred sphingosines further include phytosphingosine (INCI name; 8th Edition) and the compounds represented by the following formulas.

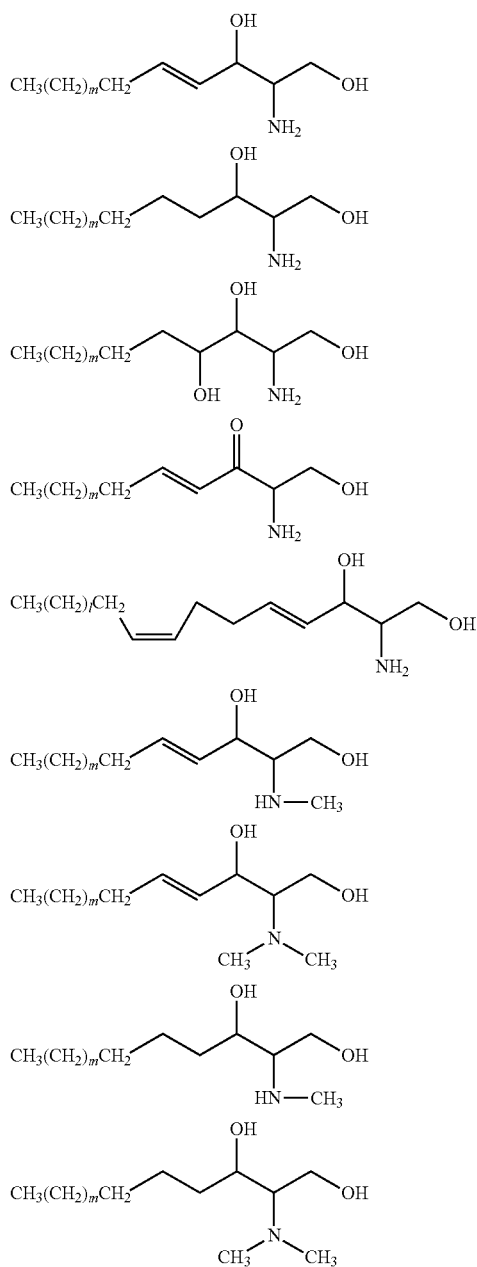

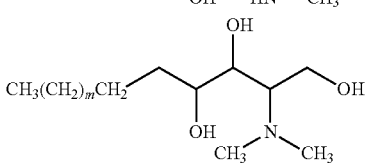

$m = 5$ to $17$, $l = 1$ to $13$

These compounds may be a natural extract or a synthetic compound, and a commercial product thereof may be used.

Examples of the commercial product of natural-type sphingosine include D-sphingosine (4-sphingenine) (product of SIGMA-ALDRICH), DS-phytosphingosine (product of DOOSAN), and phytosphingosine (product of COSMOFERM).

(II) Pseudo-sphingosine represented by formula (7)

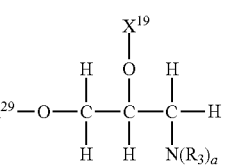

(7)

(wherein $R^{29}$ represents a C10 to C22 linear, branched, or cyclic, saturated or unsaturated hydrocarbon group which may be substituted by a hydroxyl group; $X^{19}$ represents a hydrogen atom, an acetyl group, or a glyceryl group; each of the "a" groups of $R_3$s represents a hydrogen atom, an amidino group, or a linear or branched, saturated or unsaturated hydrocarbon group optionally having a substituent selected from the group consisting of a hydroxyl group, a hydroxyalkoxy group, an alkoxy group, and an acetoxy group and containing 1 to 8 carbon atoms in total, and a is a number of 2 or 3).

In formula (7), $R^{29}$ is preferably a C14 to C20 iso-type branched alkyl group, more preferably an isostearyl group. The isostearyl group is preferably an isostearyl group derived from a raw material oil; i.e., isostearyl alcohol which is a by-product obtained in production of dimeric acid from a fatty acid originating from animal or vegetable oil.

When a is 2, $R_3$ represents $R^{30}$ and $R^{31}$, whereas when a is 3, $R_3$ represents $R^{30}$, $R^{31}$, and $R^{32}$.

Examples of the groups $R^{30}$, $R^{31}$, and $R^{32}$ include a hydrogen atom; linear or branched alkyl groups such as methyl, ethyl, propyl, 2-ethylhexyl, and isopropyl; alkenyl groups such as vinyl and allyl; an amidino group; and alkyl groups having 1 to 8 carbon atoms in total and a substituent selected from the group consisting of hydroxyl groups such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl, hydroxyalkoxy groups, and alkoxy groups.

Among them, preferred is a secondary amine in which one of $R^{30}$ and $R^{31}$ is a hydrogen atom, and the other is 2-hydroxyethyl, 1,1-dimethyl-2-hydroxyethyl, 1,1-bis(hydroxymethyl) ethyl, or 2-(2-hydroxyethoxy)ethyl.

The pseudo-sphingosine is preferably one in which $R^{29}$ is an isostearyl group, $X^{19}$ is a hydrogen atom, $R^{30}$ is a hydrogen atom, and $R^{31}$ is an alkyl group which is substituted by 1 to 3 substituents selected from the group consisting of hydroxyl groups such as 2-hydroxyethyl, 1,1-bis(hydroxymethyl) ethyl, 1,1-dimethyl-2-hydroxyethyl, and 2-(2-hydroxyethoxy)ethyl and hydroxyalkoxy groups.

Specific examples of the pseudo-sphingosine include the following pseudo-sphingosines (i) to (iv).

gosine salt, preferred are sodium methyl stearoyl taurate (N-stearoyl-N-methyltaurine sodium salt), sodium polyoxyethylene stearyl ether phosphate, arginine N-stearoyl-L-glutamate, phytosphingosine glutamic acid salt, and pseudo-sphingosine glutamic acid salt, since these compounds form a stable emulsion in a small amount of addition thereof.

One or more species of ingredient (D) may be used. The content of ingredient (D) is 0.00012 to 10 wt. %. Preferably, the content of ingredient (D) is 0.01 to 7 wt. %, more preferably 0.2 to 3 wt. %, in the total composition, since the interlayer spacing of the lamellar structure formed from ingredi-

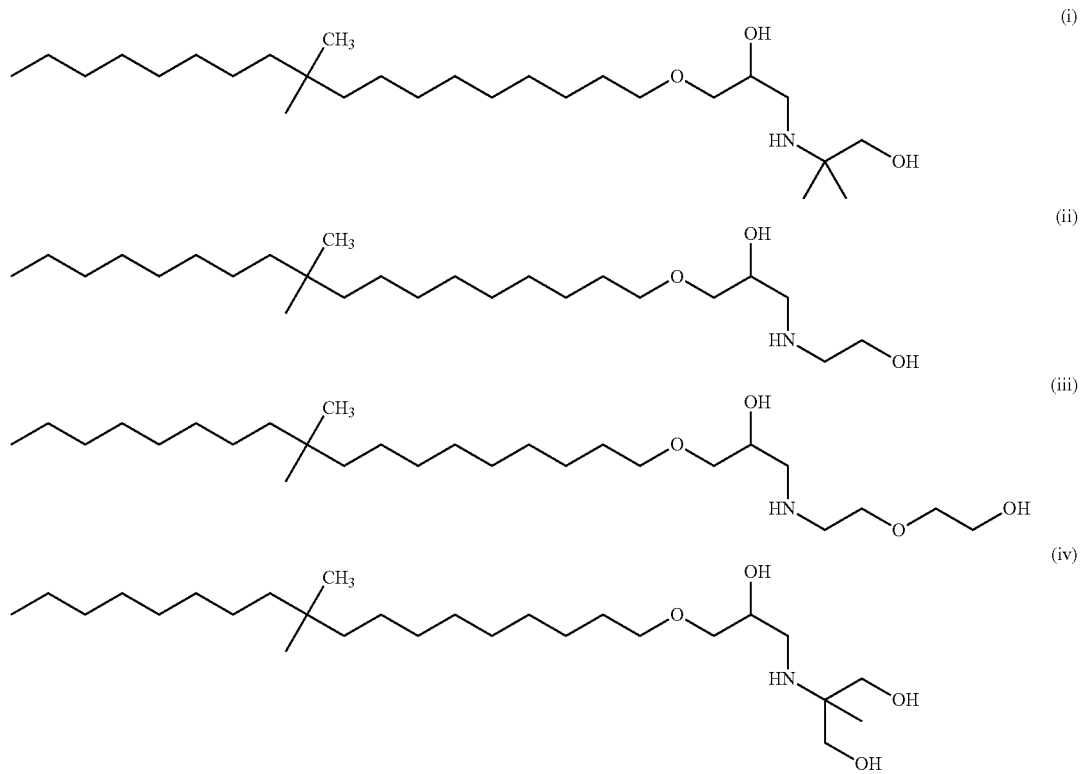

The sphingosine is preferably sphingosine, phytosphingosine, or pseudo-sphingosine, more preferably pseud-sphingosine (ii) or 1-(2-hydroxyethylamino)-3-isostearyloxy-2-propanol.

Examples of the acidic substance which forms salts with the aforementioned sphingosines, phytosphingosines, and pseudo-sphingosines include acidic amino acids such as glutamic acid and aspartic acid; inorganic acids such as phosphoric acid and hydrochloric acid; monocarboxylic acids such as acetic acid; dicarboxylic acids such as succinic acid; and hydroxycarboxylic acids such as citric acid, lactic acid, and malic acid. Among the aforementioned salts, salts of sphingosines, phytosphingosines, and pseudo-sphingosines (pseudo-sphingosine (ii), 1-(2-hydroxyethylamino)-3-isostearyloxy-2-propanol) with succinic acid, lactic acid, and glutamic acid are preferred, with glutamic acid salts of sphingosines, phytosphingosines, and pseudo-sphingosines being more preferred.

As ingredient (D), an anionic surfactant or a sphingosine salt is preferably used, since repulsion between electric charges results in retention of a large amount of water in interlayer spaces of the lamellar structure, leading to high water retention. Among the anionic surfactant and the sphinents (A), (B), and (C) can be increased, to thereby form such a structure that a large amount of water can be retained in interlayer spaces.

[Ingredient (E)]

The sugar alcohol serving as ingredient (E) of the present invention is selected from the group consisting of erythritol, threitol, xylitol, and mannitol. Of these, xylitol is preferred.

Examples of disaccharide and trisaccharide include trehalose, galactosylfructose, sucralose, melibiose, raffinose, and lactose. Of these, trehalose and raffinose are preferred, with trehalose being more preferred.

One or more species of ingredient (E) may be used. That is, sugar alcohol, disaccharide, and/or trisaccharide may be used in combination.

The content of ingredient (E) is 0.003 to 15 wt. %, in the total composition, from the viewpoint of attaining satisfactorily high water retention.

In the case of sugar alcohol, the content of sugar alcohol is preferably 0.003 to 10 wt. %, more preferably 0.01 to 5 wt. %, even more preferably 0.1 to 3 wt. %, in the total composition.

In the case of disaccharide or trisaccharide, the content of disaccharide or trisaccharide is preferably 0.018 to 15 wt. %, more preferably 0.1 to 10 wt. %, even more preferably 0.5 to 7 wt. %, in the total composition.

In the present invention, a preferable relationship of the weight ratio of ingredients (A), (B), (C) and (E) is (E)/((A)+(B)+(C)) (by weight) being preferably 0.01 to 5, since water (bound water and free water) can be firmly retained in interlayer spaces of the structure formed from ingredients (A), (B), (C), and (D), thereby remarkably enhancing water retention.

In the case where ingredient (E) is sugar alcohol, (E)/((A)+(B)+(C)) is preferably 0.01 to 3, more preferably 0.125 to 2.5. In the case of disaccharide or trisaccharide, (E)/((A)+(B)+(C)) is preferably 0.2 or more, more preferably 0.6 to 5.

Incorporation of ingredient (E) into the composition of the invention is preferred, since the lamellar structure formed from ingredients (A), (B), and (C) is stabilized, and the composition forms, on the dried skin, a soft coating layer having the same lamellar structure as the intercellular lamellar structure, whereby the skin water retention can be enhanced, to thereby provide users with long-lasting moistness.

(D)/((A)+(B)+(C)) is preferably 0.04 to 1, more preferably 0.04 to 0.5, since ingredient (C) permeability can be enhanced, whereby a moisturizing effect can be attained at the skin surface and the inside of the skin.

In the present invention, the composition preferably has an ingredient (F) (i.e., water) content of 20 to 99.9 wt. %, more preferably 40 to 95 wt. %, even more preferably 50 to 90 wt. %.

The composition of the present invention may further contain other aqueous base materials, for example, a C1 to C4 lower alcohol such as ethanol or propanol.

In the present invention, more preferably, the aforementioned preferred ingredients are employed in combination in the aforementioned preferred amounts.

In more preferred embodiment, the composition contains glyceryl monobehenate or monocetyl glyceryl ether as ingredient (A), cetanol as ingredient (B), a compound represented by formula (2) as ingredient (C), stearoylglutamic acid salt or sphingosine salt as ingredient (D), xylitol as ingredient (E), and water as ingredient (F).

The emulsion composition of the present invention may further contain an oily ingredient. Examples of the oily ingredient include hydrocarbon oils such as liquid paraffin, squalane, and petrolatum; ether oils such as cetyl dimethylbutyl ether, ethylene glycol dioctyl ether, and glycerol monooleyl ether; ester oils such as octyl dodeyl myristate, isopropyl palmitate, butyl stearate, di-2-ethylhexyl adipate, neopentyl glycol dicaprate, and trioctanoin; higher fatty acids such as stearic acid, behenic acid, and isomyristic acid; vegetable oil such as olive oil; silicone oils such as dimethylpolysiloxane, cyclic dimethylpolysiloxane, methylphenylpolysiloxane, amino-modified silicone, carboxy-modified silicone, alcohol-modified silicone, alkyl-modified silicone, polyether-modified silicone, and fluorine-modified silicone; and fluorine-containing oils such as perfluoroalkylethylphosphoric acid, perfluoroalkylpolyoxyethylenephosphoric acid, perfluoropolyether, and polytetrafluoroethylene. The composition of the invention preferably has an oily ingredient content of 0 to 20 wt. % in the total composition.

The emulsion composition of the present invention may further contain active ingredients or additives which are employed in typical cosmetics. Examples of such ingredients and additives include water-soluble vitamins such as ascorbic acid, nicotinamide, and nicotinic acid; animal and vegetable extracts such as Phellodendoron Amurense extract, licorice extract, aloe extract, horsetail extract, tea extract, cucumber extract, clove extract, ginseng extract, witch hazel extract, placenta extract, seaweed extract, horse chestnut extract, Japanese citron (Yuzu) extract, thujopsis dolabrata extract, royal jelly extract, eucalyptus extract, and thujopsis dolabrata extract solution; bases such as potassium hydroxide, sodium hydroxide, triethanolamine, and sodium carbonate; acids such as citric acid, tartaric acid, lactic acid, phosphoric acid, succinic acid, and adipic acid; and thickening agents such as carboxyvinyl polymer, sodium arginate, carrageenan, carboxymethylcellulose, hydroxyethylcellulose, guar gum, xanthan gum, carboxymethylchitosan, sodium hyaluronate, oxazoline-modified silicone, N,N-dimethylaminoethyl methacrylate diethylsulfate salt-N,N-dimethylacrylamide-polyethylene glycol dimethacrylate copolymer.

The emulsion composition of the present invention may be produced through any of production methods (1) to (3):

Production method (1): emulsification through mixing ingredients (A) to (D) (in the case of the composition containing an oily ingredient, a mixture of ingredients (A) to (D) and the oily ingredient) with an aqueous phase including ingredients (E) and (F);

Production method (2): emulsification through mixing ingredients (A) to (E) (in the case of the composition containing an oily ingredient, a mixture of ingredients (A) to (E) and the oily ingredient) with an aqueous phase including ingredient (F); and Production method (3): emulsification through mixing a mixture of ingredients (A) to (D) (in the case of the composition containing an oily ingredient, a mixture of ingredients (A) to (D) and the oily ingredient) and a portion of ingredient (E) with an aqueous phase including the remaining ingredient (E) and ingredient (F).

Production method (2) is more preferred as compared with production method (1), since the emulsion composition produced through production method (2) has higher water retention.

The thus-produced emulsion composition assumes α-gel (α-type crystal), with deposition of γ-type crystals being prevented. α-Gel can be identified through X-ray structure analysis. α-Type structure is a hexagonal crystal structure type, in which a lipophilic group is arranged normal to the hydrophilic group layer, with one characteristic diffraction peak at a Bragg angle of 21 to 23°.

Also, the emulsion composition of the present invention is an O/W-type emulsion composition and is suited for producing, for example, cosmetics such as skin lotion, milky lotion, cream, and gel, or an agent for skin external use.

EXAMPLES

Examples 1 to 10 and Comparative Examples 1 to 8

O/W emulsion compositions having formulations shown in Tables 1 and 2 were produced. The thus-produced compositions were subjected to X-ray structural analysis and remaining water content measurement. Also, the film formability of each composition was assessed. The results are also shown in Tables 1 and 2.

Through observation under a transmission electron microscope, the coating films produced in the Examples were found to have a lamellar structure.

Production Method
Production Method (1)

Phase I ingredients (mixture containing ingredients (A) to (D)) were heated and mixed at 80 to 95° C. Under propeller-stirring (300 rpm), phase II ingredients (mixture containing ingredients (E) and (F)), which had been heated to 80 to 95° C., were added to the phase I ingredients, to thereby form an emulsion. The emulsion was gradually cooled to 25° C., to thereby yield an O/W emulsion composition.

Evaluation Method (1) X-Ray Structure Analysis

The crystal structure of each of the thus-prepared O/W emulsion compositions was determined from wide angle X-ray diffraction peaks (2θ=10 to 30°) according to Wilson's & Ott's method (Wilson, D. A. and Ott, E., J. Chem. Phys., 2, 231-238(1934)).

(2) Remaining Water Content Measurement:

Each O/W emulsion composition (2 g) was spread on a metal tray (6×6 cm), to thereby form a layer having a uniform thickness. Under constant temperature and humidity conditions (25° C., 40%), the weight of the layer was monitored. The measurements were plotted to time. As shown in FIG. 1, the drawn curve was bent at two points. When a lamellar film is formed, the subsequent change in weight will be minimized. The weight value at the crossing between lines 1 and 2 in FIG. 1 was employed as the remaining water content. The water content of the solid of each composition (preparation) was calculated by the following equation (the solid containing ingredients (A) to (E)):

Water content (%)=(remaining water content/(solid content+remaining water content))×100

(3) Film Formability:

Each agent (5 g) was placed in a Petri dish (diameter: 5 cm) made of Teflon (registered trademark), and uniformly spread. The agent was dried for two days, and the state of the film was observed.

A: Formation of soft coating film
B: Formation of hard and fragile coating film
C: Formation of coating film failed

TABLE 1

|  |  | Ingredients (wt. %) | Ex. 1 | Ex. 2 | Ex. 3 | Ex. 4 | Comp. Ex. 1 | Comp. Ex. 2 | Comp. Ex. 3 | Comp. Ex. 4 |
|---|---|---|---|---|---|---|---|---|---|---|
| Phase I | D | 1-(2-Hydroxyethylamino)-3-isostearyloxy-2-propanol | 0.2 | 0.2 | 0.2 | 0.2 | 0.2 | 0.2 | 0.2 | 0.2 |
|  | C | Pseudo-ceramide* | 3 | 3 | 3 | 3 | 3 | 3 | 3 | 3 |
|  | B | Cetanol | 1 | 1 | 1 | 1 | 1 | 1 | 1 | 1 |
|  | A | Monocetyl glyceryl ether | 1 | 1 | 1 | 1 | 1 | 1 | 1 | 1 |
| Phase II | F | Water | bal. | bal. | bal. | bal. | bal. | bal. | bal. | bal. |
|  |  | L-Glutamic acid | 0.12 | 0.12 | 0.12 | 0.12 | 0.12 | 0.12 | 0.12 | 0.12 |
|  | E | Erythritol | 1 |  |  |  |  |  |  |  |
|  |  | Threitol |  | 1 |  |  |  |  |  |  |
|  |  | Xylitol |  |  | 1 |  |  |  |  |  |
|  |  | Mannitol |  |  |  | 1 |  |  |  |  |
|  |  | Sorbitol |  |  |  |  |  | 1 |  |  |
|  |  | Glycerin |  |  |  |  |  |  | 1 |  |
|  |  | Glucose |  |  |  |  |  |  |  | 1 |
| Total |  |  | 100 | 100 | 100 | 100 | 100 | 100 | 100 | 100 |
| ((A) + (B))/((A) + (B) + (C)) |  |  | 0.4 | 0.4 | 0.4 | 0.4 | 0.4 | 0.4 | 0.4 | 0.4 |
| (A)/((A) + (B)) |  |  | 0.5 | 0.5 | 0.5 | 0.5 | 0.5 | 0.5 | 0.5 | 0.5 |
| (E)/((A) + (B) + (C)) |  |  | 0.2 | 0.2 | 0.2 | 0.2 | — | — | — | — |
| X-ray structure analysis |  |  | α-type | α-type | α-type | α-type | α-type | α-type | α-type | α-type |
| Remaining water content (%) |  |  | 67.0 | 66.8 | 70.0 | 66.0 | 65.2 | 61.9 | 59.5 | 62.3 |
| Film formability |  |  | A | A | A | A | B | B | B | B |

*N-(Hexadecyloxyhydroxypropyl)-N-hydroxyethylhexadecanamide

TABLE 2

|  |  | Ingredients (wt. %) | Ex. 5 | Ex. 6 | Ex. 7 | Ex. 8 | Ex. 9 | Ex. 10 | Comp. Ex. 5 | Comp. Ex. 6 | Comp. Ex. 7 | Comp. Ex. 8 |
|---|---|---|---|---|---|---|---|---|---|---|---|---|
| Phase I | D | 1-(2-Hydroxyethylamino)-3-isostearyloxy-2-propanol | 0.2 | 0.2 | 0.2 | 0.2 | 0.2 | 0.2 | 0.2 | 0.2 | 0.2 | 0.2 |
|  | C | Pseudo-ceramide* | 3 | 3 | 3 | 3 | 3 | 3 | 3 | 3 | 3 | 3 |
|  | B | Cetanol | 1 | 1 | 1 | 1 | 1 | 1 | 1 | 1 | 1 | 1 |
|  | A | Monocetyl glyceryl ether | 1 | 1 | 1 | 1 | 1 | 1 | 1 | 1 | 1 | 1 |
| Phase II | F | Water | bal. | bal. | bal. | bal. | bal. | bal. | bal. | bal. | bal. | bal. |
|  |  | L-Glutamic acid | 0.12 | 0.12 | 0.12 | 0.12 | 0.12 | 0.12 | 0.12 | 0.12 | 0.12 | 0.12 |
|  | E | Trehalose | 5 |  |  |  |  |  |  |  |  |  |
|  |  | Raffinose |  | 5 |  |  |  |  |  |  |  |  |
|  |  | Lactose |  |  | 5 |  |  |  |  |  |  |  |
|  |  | Galactosylfructose |  |  |  | 5 |  |  |  |  |  |  |
|  |  | Sucralose |  |  |  |  | 5 |  |  |  |  |  |
|  |  | Melibiose |  |  |  |  |  | 5 |  |  |  |  |
|  |  | Glycerin |  |  |  |  |  |  | 5 |  |  |  |
|  |  | Glucose |  |  |  |  |  |  |  | 5 |  |  |
|  |  | Trimethylglycine |  |  |  |  |  |  |  |  |  | 5 |
| Total |  |  | 100 | 100 | 100 | 100 | 100 | 100 | 100 | 100 | 100 | 100 |
| ((A) + (B))/((A) + (B) + (C)) |  |  | 0.4 | 0.4 | 0.4 | 0.4 | 0.4 | 0.4 | 0.4 | 0.4 | 0.4 | 0.4 |
| (A)/((A) + (B)) |  |  | 0.5 | 0.5 | 0.5 | 0.5 | 0.5 | 0.5 | 0.5 | 0.5 | 0.5 | 0.5 |
| (E)/((A) + (B) + (C)) |  |  | 1.0 | 1.0 | 1.0 | 1.0 | 1.0 | 1.0 | — | — | — | — |
| X-ray structure analysis |  |  | α-type | α-type | α-type | α-type | α-type | α-type | α-type | α-type | α-type | α-type |

TABLE 2-continued

|  | Ex. | | | | | | Comp. Ex. | | | |
| --- | --- | --- | --- | --- | --- | --- | --- | --- | --- | --- |
| Ingredients (wt. %) | 5 | 6 | 7 | 8 | 9 | 10 | 5 | 6 | 7 | 8 |
| Remaining water content (%) | 72.15 | 71.21 | 71.21 | 70.72 | 70.28 | 71.44 | 65.20 | 53.18 | 61.50 | 59.41 |
| Film formability | A | A | A | A | A | A | B | B | B | C |

*N-(Hexadecyloxyhydroxypropyl)-N-hydroxyethylhexadecanamide

Example 11 and Comparative Examples 9 to 11

In a manner similar to that employed in Examples 1 to 10, O/W emulsion compositions having formulations shown in Table 3 were produced. The small angle X-ray scattering intensity of each composition was monitored. The intensity was compared with that of the composition of Comparative Example 9. Table 3 shows the results.

TABLE 3

| | | | Ex. | Comp. Ex. | | |
| --- | --- | --- | --- | --- | --- | --- |
| | | Ingredients (wt. %) | 11 | 9 | 10 | 11 |
| Phase I | D | 1-(2-Hydroxyethylamino)-3-isostearyloxy-2-propanol | 0.4 | 0.4 | 0.4 | 0.4 |
| | C | Pseudo-ceramide* | 6 | 6 | 6 | 6 |
| | B | Cetanol | 2 | 2 | 2 | 2 |
| | A | Monocetyl glyceryl ether | 2 | 2 | 2 | 2 |
| Phae II | F | Water | bal. | bal. | bal. | bal. |
| | | L-Glutamic acid | 0.24 | 0.24 | 0.24 | 0.24 |
| | E | Xylitol | 3 | | | |
| | | Trimethylglycine | | | 3 | |
| | | Glycerin | | | | 3 |
| Total | | | 100 | 100 | 100 | 100 |
| ((A) + (B))/((A) + (B) + (C)) | | | 0.4 | 0.4 | 0.4 | 0.4 |
| (A)/((A) + (B)) | | | 0.5 | 0.5 | 0.5 | 0.5 |
| (E)/((A) + (B) + (C)) | | | 0.3 | — | — | — |
| Small angle X-ray scattering intensity | | | increase | | no change | no change |

*N-(Hexadecyloxyhydroxypropyl)-N-hydroxyethylhexadecanamide

As is clear from Table 3, the composition of Example 11 exhibited an increase in small angle X-ray scattering intensity, indicating that the lamellar structure has high order.

Examples 12 to 17 and Comparative Examples 12 to 21

In a manner similar to that employed in Examples 1 to 10, O/W emulsion compositions having formulations shown in Table 4 were produced. The thus-produced compositions were subjected to X-ray structural analysis and evaluated in terms of remaining water content and film formability. The skin permeability of each composition and lasting of moist skin attained by the composition were assessed. The results are also shown in Table 4.

Evaluation Methods

Feeling Upon Use of the Composition (Skin Permeability/Lasting of Moist Skin)

The emulsion compositions were tested by 10 expert panelists. Specifically, each emulsion composition (0.5 to 0.6 g) was applied to the face of each panelist. The "skin permeation sensation" immediately after application of the composition and "lasting of moist skin" 10 hours after application thereof were sensorily evaluated by the panelists. The evaluation was scores represented by the number of panelists who gave a rating of "satisfactory."

TABLE 4

|  |  | Ingredients (wt. %) | Ex. 12 | Ex. 13 | Ex. 14 | Ex. 15 | Ex. 16 | Ex. 17 |
|---|---|---|---|---|---|---|---|---|
| Phase I | D | 1-(2-Hydroxyethylamino)-3-isostearyloxy-2-propanol |  |  | 0.2 | 0.2 |  |  |
|  | D | Stearoylglutamic acid | 0.5 |  |  |  |  | 0.5 |
|  | D | Sodium methyl stearoyl taurate |  |  |  | 0.5 |  |  |
|  | D | Polyoxyethylene(20) sorbitan monostearate (HLB 14.9) |  |  |  |  | 2 |  |
|  |  | Hydrogenated lecithin |  |  |  | 1 |  |  |
|  | C | Pseudo-ceramide* | 2 | 2.5 | 3 | 1 | 1 | 1 |
|  |  | Stearic acid |  |  |  |  |  |  |
|  | B | Cetanol | 1 | 1 | 1 | 1.5 | 1 | 3 |
|  | B | Cholesterol |  |  |  |  |  |  |
|  | A | Glyceryl monostearate |  |  |  |  |  |  |
|  | A | Glyceryl monobehenate |  | 1.5 |  |  |  | 1 |
|  | A | Monostearyl glyceryl ether |  |  |  | 2.5 | 3 |  |
|  | A | Monocetyl glyceryl ether | 2 |  |  |  |  |  |
|  | A | Sorbitan monostearate |  |  |  | 1 |  |  |
|  | A | Sorbitan distearate |  |  |  |  |  | 0.5 |
| Phase II | F | Water | bal. | bal. | bal. | bal. | bal. | bal. |
|  |  | L-Arginine | 0.35 |  |  |  |  |  |
|  |  | L-Glutamic acid |  | 0.12 | 0.12 |  |  |  |
|  | E | Xylitol | 1 | 1 | 1 | 1 | 1 | 1 |
| Total |  |  | 100 | 100 | 100 | 100 | 100 | 100 |
| ((A) + (B))/((A) + (B) + (C)) |  |  | 0.6 | 0.5 | 0.4 | 0.8 | 0.8 | 0.8 |
| (A)/((A) + (B)) |  |  | 0.67 | 0.6 | 0.5 | 0.63 | 0.75 | 0.3 |
| (E)/((A) + (B) + (C)) |  |  | 0.2 | 0.2 | 0.2 | 0.2 | 0.2 | 0.2 |
| X-ray structure analysis |  |  | α-type | α-type | α-type | α-type | α-type | α-type |
| Remaining water content (%) |  |  | 64.6 | 63.3 | 61.5 | 59.9 | 57.7 | 60.2 |
| Film formability |  |  | A | A | A | A | A | A |
| Permeation sensation |  |  | 10 | 10 | 9 | 9 | 8 | 8 |
| Lasting of moist skin |  |  | 10 | 9 | 9 | 8 | 7 | 8 |

|  |  | Ingredients (wt. %) | Comp. Ex. 12 | 13 | 14 | 15 | 16 | 17 | 18 | 19 | 20 | 21 |
|---|---|---|---|---|---|---|---|---|---|---|---|---|
| Phase I | D | 1-(2-Hydroxyethylamino)-3-isostearyloxy-2-propanol |  | 0.2 | 0.2 |  |  | 0.2 | 0.2 |  |  |  |
|  | D | Stearoylglutamic acid | 0.5 |  |  |  |  |  |  |  |  |  |
|  | D | Sodium methyl stearoyl taurate |  |  |  | 0.5 |  |  |  |  | 0.3 |  |
|  | D | Polyoxyethylene(20) sorbitan monostearate (HLB 14.9) |  |  |  |  | 2 |  |  | 2.3 |  |  |
|  |  | Hydrogenated lecithin |  |  |  | 1 |  |  |  |  |  | 1.5 |
|  | C | Pseudo-ceramide* | 2 | 2.5 | 3 | 1 | 1 |  | 3 |  |  |  |
|  |  | Stearic acid |  |  |  |  |  |  |  |  | 3 |  |
|  | B | Cetanol | 1 | 1 | 1 | 1.5 | 1 | 2.5 | 2 | 1.8 | 2 |  |
|  | B | Cholesterol |  |  |  |  |  | 2.5 |  |  |  | 1 |
|  | A | Glyceryl monostearate |  |  |  |  |  |  |  | 3.2 |  |  |
|  | A | Glyceryl monobehenate |  | 1.5 |  |  |  |  |  |  |  |  |
|  | A | Monostearyl glyceryl ether |  |  |  | 2.5 | 3 |  |  |  |  | 4 |
|  | A | Monocetyl glyceryl ether | 2 |  |  |  |  |  |  |  |  |  |
|  | A | Sorbitan monostearate |  |  |  | 1 |  |  |  |  |  |  |
|  | A | Sorbitan distearate |  |  |  |  |  |  |  |  |  |  |
| Phase II | F | Water | bal. | bal. | bal. | bal. | bal. | bal. | bal. | bal. | bal. | bal. |
|  |  | L-Arginine | 0.35 |  |  |  |  |  |  |  |  |  |
|  |  | L-Glutamic acid |  | 0.12 | 0.12 |  |  | 0.12 | 0.12 |  |  |  |
|  | E | Xylitol |  |  |  |  |  | 1 | 1 | 1 | 1 | 1 |
| Total |  |  | 100 | 100 | 100 | 100 | 100 | 100 | 100 | 100 | 100 | 100 |
| ((A) + (B))/((A) + (B) + (C)) |  |  | 0.6 | 0.5 | 0.4 | 0.8 | 0.8 | 1 | 0.4 | 1 | 0.4 | 1 |
| (A)/((A) + (B)) |  |  | 0.67 | 0.6 | 0.5 | 0.63 | 0.75 | — | — | 0.64 | — | 0.8 |
| (E)/((A) + (B) + (C)) |  |  | — | — | — | — | — | 0.2 | 0.2 | 0.2 | 0.2 | 0.2 |
| X-ray structure analysis |  |  | α-type | α-type | α-type | α-type | α-type | γ-type | α-type | α-type | α-type | α-type |
| Remaining water content (%) |  |  | 59.1 | 58.7 | 57.1 | 57 | 55.1 | 10.8 | 32.6 | 52.6 | 20.8 | 16.3 |
| Film formability |  |  | B | B | B | B | B | C | B | B | B | C |
| Permeation sensation |  |  | 7 | 6 | 8 | 7 | 7 | 3 | 6 | 7 | 5 | 1 |
| Lasting of moist skin |  |  | 6 | 4 | 5 | 4 | 4 | 3 | 5 | 4 | 3 | 2 |

*N-(Hexadecyloxyhydroxypropyl)-N-hydroxyethylhexadecanamide

Examples 18 to 53 and Comparative Examples 22 to 33

In a manner similar to that employed in Examples 1 to 10, O/W emulsion compositions having formulations shown in Tables 5 to 9 were produced. The thus-produced compositions were subjected to X-ray structural analysis and evaluated in terms of remaining water content. The skin permeability and lasting of moist skin attained by each composition were assessed. The results are also shown in Tables 5 to 9.

TABLE 5

| | | Ingredients (wt. %) | Ex. 18 | Ex. 19 | Ex. 20 | Ex. 21 | Ex. 22 |
|---|---|---|---|---|---|---|---|
| Phase I | D | 1-(2-Hydroxyethylamino)-3-isostearyloxy-2-propanol | | 0.2 | 0.2 | | |
| | D | Stearoylglutamic acid | 0.5 | | | | |
| | D | Sorium methyl stearoyl taurate | | | | 0.5 | |
| | D | Polyoxyethylene(20) sorbitan monostearate (HLB 14.9) | | | | | 2 |
| | | Hydrogenated lecithin | | | | 1 | |
| | C | Pseudo-ceramide* | 2 | 2.5 | 3 | 1 | 1 |
| | | Stearic acid | | | | | |
| | B | Cetanol | 1 | 1 | 1 | 1.5 | 1 |
| | B | Cholesterol | | | | | |
| | A | Glyceryl monostearate | | | | | |
| | A | Glyceryl monobehenate | | 1.5 | | | |
| | A | Monostearyl glyceryl ether | | | | 2.5 | 3 |
| | A | Monocetyl glyceryl ether | 2 | | | | |
| | A | Sorbitan monostearate | | | 1 | | |
| Phase II | F | Water | bal. | bal. | bal. | bal. | bal. |
| | | L-Arginine | 0.35 | | | | |
| | | L-Glutamic acid | | 0.12 | 0.12 | | |
| | E | Trehalose | 5 | 5 | 5 | 5 | 5 |
| Total | | | 100 | 100 | 100 | 100 | 100 |
| ((A) + (B))/((A) + (B) + (C)) | | | 0.6 | 0.5 | 0.4 | 0.8 | 0.8 |
| (A)/((A) + (B)) | | | 0.7 | 0.6 | 0.5 | 0.6 | 0.8 |
| (E)/((A) + (B) + (C)) | | | 1.0 | 1.0 | 1.0 | 1.0 | 1.0 |
| X-ray structure analysis | | | α-type | α-type | α-type | α-type | α-type |
| Remaining water content (%) | | | 67.53 | 67.58 | 66.25 | 62.97 | 60.50 |
| Permeation sensation | | | 9 | 9 | 9 | 8 | 8 |
| Lasting of moist skin | | | 10 | 9 | 9 | 8 | 6 |

| | | Ingredients (wt. %) | Comp. Ex. 22 | 23 | 24 | 25 | 26 | 27 | 28 | 29 | 30 | 31 |
|---|---|---|---|---|---|---|---|---|---|---|---|---|
| Phase I | D | 1-(2-Hydroxyethylamino)-3-isostearyloxy-2-propanol | | 0.2 | 0.2 | | | 0.2 | 0.2 | | | |
| | D | Stearoylglutamic acid | 0.5 | | | | | | | | | |
| | D | Sorium methyl stearoyl taurate | | | | 0.5 | | | | | 0.3 | |
| | D | Polyoxyethylene(20) sorbitan monostearate (HLB 14.9) | | | | | 2 | | | | 2.3 | |
| | | Hydrogenated lecithin | | | | 1 | | | | | | 1.5 |
| | C | Pseudo-ceramide* | 2 | 2.5 | 3 | 1 | 1 | | 3 | | | |
| | | Stearic acid | | | | | | | | | 3 | |
| | B | Cetanol | 1 | 1 | 1 | 1.5 | 1 | 2.5 | 2 | 1.8 | 2 | |
| | B | Cholesterol | | | | | | 2.5 | | | | 1 |
| | A | Glyceryl monostearate | | | | | | | | 3.2 | | |
| | A | Glyceryl monobehenate | | 1.5 | | | | | | | | |
| | A | Monostearyl glyceryl ether | | | | 2.5 | 3 | | | | | 4 |
| | A | Monocetyl glyceryl ether | 2 | | | | | | | | | |
| | A | Sorbitan monostearate | | | 1 | | | | | | | |
| Phase II | F | Water | bal. | bal. | bal. | bal. | bal. | bal. | bal. | bal. | bal. | bal. |
| | | L-Arginine | 0.35 | | | | | | | | | |
| | | L-Glutamic acid | | 0.12 | 0.12 | | | 0.12 | 0.12 | | | |
| | E | Trehalose | | | | | 5 | 5 | 5 | 5 | 5 | 5 |
| Total | | | 100 | 100 | 100 | 100 | 100 | 100 | 100 | 100 | 100 | 100 |
| ((A) + (B))/((A) + (B) + (C)) | | | 0.6 | 0.5 | 0.4 | 0.8 | 0.8 | — | 0.7 | 1.0 | — | 1.0 |
| (A)/((A) + (B)) | | | 0.7 | 0.6 | 0.5 | 0.6 | 0.8 | — | — | 0.6 | — | 0.8 |
| (E)/((A) + (B) + (C)) | | | — | — | — | — | — | 1.0 | 1.7 | 1.0 | 2.5 | 1.0 |
| X-ray structure analysis | | | α-type | α-type | α-type | α-type | α-type | γ-type | α-type | α-type | α-type | α-type |
| Remaining water content (%) | | | 59.13 | 58.65 | 57.13 | 56.99 | 55.10 | 24.32 | 41.35 | 56.04 | 28.50 | 23.04 |
| Permeation sensation | | | 7 | 6 | 8 | 7 | 7 | 3 | 6 | 2 | 4 | 7 |
| Lasting of moist skin | | | 5 | 5 | 4 | 4 | 4 | 8 | 4 | 1 | 4 | 1 |

*N-(Hexadecyloxyhydroxypropyl)-N-hydroxyethylhexadecanamide

TABLE 6

|   |   | Ingredients (wt. %) | Ex. 23 | Ex. 24 | Ex. 25 | Ex. 26 | Ex. 27 | Ex. 28 | Ex. 29 | Ex. 30 | Ex. 31 | Comp. Ex. 32 |
|---|---|---|---|---|---|---|---|---|---|---|---|---|
| Phase I | D | 1-(2-Hydroxyethylamino)-3-isostearyloxy-2-propanol | 0.13 | 0.25 | 0.1 | 0.2 | 2 | 0.25 | 0.2 | 0.4 | 1.2 | 0.2 |
|   | C | Pseudo-ceramide* | 2.8 | 4 | 1 | 3 | 0.5 | 0.1 | 0.1 | 0.2 | 0.2 | 11 |
|   | B | Cetanol | 0.45 | 1.6 | 0.5 | 1 | 1 | 0.1 | 1 | 0.4 | 0.4 | 0.5 |
|   | A | Glyceryl monobehenate | 0.05 | 0.55 | 0.5 | 1 | 0.5 | 0.3 | 1 | 0.4 | 0.4 | 0.05 |
| Phase II | F | Water | bal. | bal. | bal. | bal. | bal. | bal. | bal. | bal. | bal. | bal. |
|   |   | L-Glutamic acid | 0.078 | 0.15 | 0.06 | 0.12 | 1.2 | 0.15 | 0.12 | 0.24 | 0.72 | 0.12 |
|   | E | Xylitol | 0.04 | 0.8 | 1 | 1 | 3 | 1.25 | 1 | 3 | 3 | 0.04 |
| Total |   |   | 100 | 100 | 100 | 100 | 100 | 100 | 100 | 100 | 100 | 100 |
| ((A) + (B))/((A) + (B) + (C)) |   |   | 0.15 | 0.35 | 0.5 | 0.4 | 0.8 | 0.8 | 0.95 | 0.8 | 0.8 | 0.05 |
| (A)/((A) + (B)) |   |   | 0.1 | 0.26 | 0.5 | 0.5 | 0.33 | 0.75 | 0.5 | 0.5 | 0.5 | 0.09 |
| (E)/((A) + (B) + (C)) |   |   | 0.01 | 0.13 | 0.5 | 0.2 | 1.5 | 2.5 | 0.48 | 3.0 | 3.0 | 0.003 |
| X-ray structure analysis |   |   | α-type | α-type | α-type | α-type | α-type | α-type | α-type | α-type | α-type | γ-type |
| Remaining water content (%) |   |   | 58.1 | 59.5 | 62.9 | 61.5 | 65.3 | 60.6 | 55.0 | 57.1 | 58.2 | 13.4 |
| Film formability |   |   | A | A | A | A | A | A | A | A | A | C |
| Permeation sensation |   |   | 7 | 8 | 9 | 10 | 8 | 9 | 8 | 7 | 7 | 4 |
| Lasting of moist skin |   |   | 7 | 9 | 10 | 10 | 10 | 8 | 7 | 7 | 8 | 1 |

*N-(Hexadecyloxyhydroxypropyl)-N-hydroxyethylhexadecanamide

TABLE 7

|   |   | Ingredients (wt. %) | Ex. 32 | Ex. 33 | Ex. 34 | Ex. 35 | Ex. 36 | Ex. 37 | Ex. 38 | Ex. 39 | Ex. 40 | Comp. Ex. 33 |
|---|---|---|---|---|---|---|---|---|---|---|---|---|
| Phase I | D | 1-(2-Hydroxyethylamino)-3-isostearyloxy-2-propanol | 0.13 | 0.25 | 0.1 | 0.5 | 2 | 0.25 | 0.2 | 0.2 | 1.2 | 0.2 |
|   | C | Pseudo-ceramide* | 2.8 | 4 | 1 | 3 | 0.5 | 0.1 | 0.1 | 0.2 | 0.2 | 11 |
|   | B | Cetanol | 0.45 | 1.6 | 0.5 | 1 | 1 | 0.1 | 1 | 0.4 | 0.4 | 0.5 |
|   | A | Glyceryl monobehenate | 0.05 | 0.55 | 0.5 | 1 | 0.5 | 0.3 | 1 | 0.4 | 0.4 | 0.05 |
| Phase II | F | Water | bal. | bal. | bal. | bal. | bal. | bal. | bal. | bal. | bal. | bal. |
|   |   | L-Glutamic acid | 0.078 | 0.15 | 0.06 | 0.12 | 1.2 | 0.15 | 0.12 | 0.12 | 0.72 | 0.12 |
|   | E | Trehalose | 0.7 | 3.7 | 2 | 4 | 3 | 2.5 | 2 | 4 | 3 | 0.04 |
| Total |   |   | 100 | 100 | 100 | 100 | 100 | 100 | 100 | 100 | 100 | 100 |
| ((A) + (B))/((A) + (B) + (C)) |   |   | 0.15 | 0.35 | 0.5 | 0.4 | 0.8 | 0.8 | 0.95 | 0.8 | 0.8 | 0.07 |
| (A)/((A) + (B)) |   |   | 0.1 | 0.26 | 0.5 | 0.5 | 0.33 | 0.75 | 0.5 | 0.5 | 0.5 | 0.09 |
| (E)/((A) + (B) + (C)) |   |   | 0.21 | 0.60 | 1.0 | 0.8 | 1.5 | 5.0 | 0.95 | 4.0 | 3.0 | 0.003 |
| X-ray structure analysis |   |   | α-type | α-type | α-type | α-type | α-type | α-type | α-type | α-type | α-type | γ-type |
| Remaining water content (%) |   |   | 57.4 | 60.2 | 63.3 | 67.2 | 66.9 | 61.7 | 55.5 | 62.5 | 61.1 | 14.8 |
| Film formability |   |   | A | A | A | A | A | A | A | A | A | C |
| Permeation sensation |   |   | 7 | 8 | 10 | 10 | 8 | 9 | 7 | 7 | 7 | 5 |
| Lasting of moist skin |   |   | 7 | 9 | 10 | 10 | 9 | 8 | 7 | 8 | 8 | 3 |

*N-(Hexadecyloxyhydroxypropyl)-N-hydroxyethylhexadecanamide

TABLE 8

|   |   | Ingredients (wt. %) | Ex. 41 | Ex. 42 | Ex. 43 | Ex. 44 | Ex. 45 |
|---|---|---|---|---|---|---|---|
| Phase I | D | 1-(2-Hydroxyethylamino)-3-isostearyloxy-2-propanol | 0.01 | 0.2 | 3 | 7 | 10 |
|   | C | Pseudo-ceramide* | 0.05 | 0.1 | 5 | 7 | 10 |
|   | B | Cetanol | 0.05 | 0.1 | 3 | 7 | 10 |
|   | A | Glyceryl monobehenate | 0.05 | 0.3 | 3 | 7 | 10 |
| Phase II | F | Water | bal. | bal. | bal. | bal. | bal. |
|   |   | L-Glutamic acid | 0.006 | 0.12 | 1.8 | 4.2 | 6 |
|   | E | Xylitol | 0.01 | 0.1 | 3 | 5 | 10 |
| Total |   |   | 100 | 100 | 100 | 100 | 100 |
| ((A) + (B))/((A) + (B) + (C)) |   |   | 0.67 | 0.8 | 0.55 | 0.67 | 0.67 |
| (A)/((A) + (B)) |   |   | 0.5 | 0.75 | 0.5 | 0.5 | 0.5 |
| (E)/((A) + (B) + (C)) |   |   | 0.07 | 0.2 | 0.27 | 0.24 | 0.33 |
| X-ray structure analysis |   |   | α-type | α-type | α-type | α-type | α-type |
| Remaining water content (%) |   |   | 60.3 | 65.1 | 67.8 | 60.5 | 54.3 |
| Film formability |   |   | A | A | A | A | B |

TABLE 8-continued

|  | Ex. | | | | |
| --- | --- | --- | --- | --- | --- |
| Ingredients (wt. %) | 41 | 42 | 43 | 44 | 45 |
| Permeation sensation | 7 | 9 | 9 | 9 | 7 |
| Lasting of moist skin | 9 | 9 | 10 | 8 | 6 |

*N-(Hexadecyloxyhydroxypropyl)-N-hydroxyethylhexadecanamide

TABLE 9

| | | Ingredients (wt. %) | Ex. | | | | | | | |
| --- | --- | --- | --- | --- | --- | --- | --- | --- | --- | --- |
| | | | 46 | 47 | 48 | 49 | 50 | 51 | 52 | 53 |
| Phase I | D | 1-(2-Hydroxyethylamino)-3-isostearyloxy-2-propanol | 0.01 | 0.2 | 1 | 3 | 3 | 7 | 3 | 7 |
| | C | Pseudo-ceramide* | 0.05 | 0.1 | 1 | 5 | 5 | 7 | 5 | 10 |
| | B | Cetanol | 0.05 | 0.1 | 1 | 3 | 3 | 7 | 3 | 10 |
| | A | Glyceryl monobehenate | 0.05 | 0.3 | 1 | 3 | 5 | 7 | 3 | 10 |
| Phase II | F | Water | bal. | bal. | bal. | bal. | bal. | bal. | bal. | bal. |
| | | L-Glutamic acid | 0.006 | 0.12 | 0.6 | 1.8 | 1.8 | 4.2 | 1.8 | 4.2 |
| | E | Trehalose | 0.1 | 0.5 | 3 | 7 | 10 | 10 | 15 | 6 |
| Total | | | 100 | 100 | 100 | 100 | 100 | 100 | 100 | 100 |
| ((A) + (B))/((A) + (B) + (C)) | | | 0.67 | 0.8 | 0.67 | 0.55 | 0.62 | 0.67 | 0.55 | 0.67 |
| (A)/((A) + (B)) | | | 0.5 | 0.75 | 0.5 | 0.5 | 0.63 | 0.5 | 0.5 | 0.5 |
| (E)/((A) + (B) + (C)) | | | 0.67 | 1.0 | 1.0 | 0.64 | 0.77 | 0.48 | 1.36 | 0.2 |
| X-ray structure analysis | | | α-type | α-type | α-type | α-type | α-type | α-type | α-type | α-type |
| Remaining water content (%) | | | 65.8 | 67.7 | 69.3 | 68.0 | 67.5 | 61.2 | 57.3 | 55.4 |
| Film formability | | | A | A | A | A | A | A | A | B |
| Permeation sensation | | | 7 | 10 | 10 | 10 | 8 | 7 | 6 | 7 |
| Lasting of moist skin | | | 7 | 9 | 10 | 9 | 9 | 8 | 7 | 5 |

*N-(Hexadecyloxyhydroxypropyl)-N-hydroxyethylhexadecanamide

Examples 54 to 56

O/W emulsion compositions having formulations shown in Table 10 were produced through production method (2). The thus-produced emulsion compositions were subjected to X-ray structural analysis and evaluated in terms of remaining water content and film formability. The skin permeability of each composition and lasting of moist skin attained by each composition were assessed. The results are also shown in Table 10.

Emulsion compositions having the same formulations as those of Examples 54 to 56 were also produced through production method (1) (Examples 30, 3, and 5). The evaluation results thereof are also shown in Table 10.

Production Method (2)

Phase I ingredients (mixture containing ingredients (A) to (E)) were heated and mixed at 80 to 95° C. Under propeller-stirring (300 rpm), phase II ingredient (aqueous phase containing ingredient (F)), which had been heated to 80 to 95° C., was added to the phase I ingredients, to thereby form an emulsion. The emulsion was gradually cooled to 25° C., to thereby yield an O/W emulsion composition.

TABLE 10

| | | Ingredients (wt. %) | Ex. | | | | | |
| --- | --- | --- | --- | --- | --- | --- | --- | --- |
| | | | 54 | 30 | 55 | 3 | 56 | 5 |
| Phase I | D | 1-(2-Hydroxyethylamino)-3-isostearyloxy-2-propanol | 0.4 | 0.4 | 0.2 | 0.2 | 0.2 | 0.2 |
| | C | Pseudo-ceramide* | 0.2 | 0.2 | 3 | 3 | 3 | 3 |
| | B | Cetanol | 0.4 | 0.4 | 1 | 1 | 1 | 1 |
| | A | Glyceryl monobehenate | 0.4 | 0.4 | | | | |
| | A | Monocetyl glyceryl ether | | | 1 | 1 | 1 | 1 |
| | E | Xylitol | 3 | | 1 | | | |
| | E | Trehalose | | | | | 5 | |
| Phase II | F | Water | bal. | bal. | bal. | bal. | bal. | bal. |
| | | L-Glutamic acid | 0.24 | 0.24 | 0.12 | 0.12 | 0.12 | 0.12 |
| | E | Xylitol | | 3 | | 1 | | |
| | E | Trehalose | | | | | | 5 |
| Total | | | 100 | 100 | 100 | 100 | 100 | 100 |
| ((A) + (B))/((A) + (B) + (C)) | | | 0.8 | 0.8 | 0.4 | 0.4 | 0.4 | 0.4 |
| (A)/((A) + (B)) | | | 0.5 | 0.5 | 0.5 | 0.5 | 0.5 | 0.5 |
| (E)/((A) + (B) + (C)) | | | 3.0 | 3.0 | 0.2 | 0.2 | 0.2 | 1.0 |
| X-ray structure analysis | | | α-type | α-type | α-type | α-type | α-type | α-type |
| Remaining water content (%) | | | 59.6 | 57.1 | 71.0 | 70.0 | 74.6 | 72.15 |
| Film formability | | | A | A | A | A | A | A |

TABLE 10-continued

| | Ex. | | | | | |
|---|---|---|---|---|---|---|
| Ingredients (wt. %) | 54 | 30 | 55 | 3 | 56 | 5 |
| Permeation sensation | 8 | 7 | 10 | 8 | 10 | 7 |
| Lasting of moist skin | 9 | 7 | 10 | 9 | 10 | 9 |

*N-(hexadecyloxyhydroxypropyl)-N-hydroxyethylhexadecanamide

Example 57

Skin Lotion

In a manner similar to that employed in Examples 1 to 10, an O/W emulsion composition (skin lotion) having a formulation shown in Table 11 was produced. X-ray structural analysis of the composition was performed. Film formability, and skin permeability of the composition, and lasting of moist skin attained by the composition were assessed. The results are also shown in Table 11.

TABLE 11

| | | (Ingredients) | (wt. %) |
|---|---|---|---|
| Phase I | D | 1-(2-Hydroxyethylamino)-3-isostearyloxy-2-propanol | 0.2 |
| | D | Phytosphingosine | 0.01 |
| | C | Pseudo-ceramide* | 0.5 |
| | C | CERAMIDE 2 | 0.1 |
| | B | Cetanol | 0.2 |
| | A | Monostrearyl glyceryl ether | 0.2 |
| | | Glycerin | 5.0 |
| Phase II | F | Water | bal. |
| | | Methylparaben | q.s. |
| | E | Xylitol | 1.0 |
| | E | Erythritol | 1.0 |
| | | Hydroxyethylcellulose | 0.01 |
| | | *Eucalyptus* extract | 0.1 |
| | | *Thujopsis dolabrata* extract | 0.1 |
| | | Altheae extract | 0.1 |
| | | Seaweed extract | 0.1 |
| | | L-Glutamic acid | 0.1 |
| Total | | | 100 |
| ((A) + (B))/((A) + (B) + (C)) | | | 0.40 |
| (A)/((A) + (B)) | | | 0.50 |
| (E)/((A) + (B) + (C)) | | | 1.98 |
| X-ray structure analysis | | | α-type |
| Film formability | | | A |
| Permeation sensation | | | 8 |
| Lasting of moist skin | | | 8 |

*N-(Hexadecyloxyhydroxypropyl)-N-hydroxyethylhexadecanamide

Example 58

Milky Lotion

In a manner similar to that employed in Examples 1 to 10, an O/W emulsion composition (milky lotion) having a formulation shown in Table 12 was produced. X-ray structural analysis of the composition was performed. The film formability and skin permeability of the composition, and lasting of moist skin attained by the composition were assessed. The results are also shown in Table 12.

TABLE 12

| | | (Ingredients) | (wt. %) |
|---|---|---|---|
| Phase I | D | Sodium polyoxyethylene(4) lauryl ether phosphate | 0.2 |
| | D | Polyoxyethylene(20) sorbitan monostearate (HLB 14.9) | 0.3 |
| | C | Pseudo-ceramide* | 1.0 |
| | C | CERAMIDE 2 | 0.1 |
| | B | Cetanol | 1.0 |
| | A | Sorbitan monostearate | 0.2 |
| | | Squalane | 4.0 |
| | | Dimethylpolysiloxane | 5.0 |
| | | Glycerin | 10.0 |
| Phase II | F | Water | bal. |
| | D | Sodium methyl stearoyl taurate | 0.3 |
| | | Methylparaben | q.s. |
| | | Phenoxyethanol | q.s. |
| | | Sodium hydroxide | q.s. |
| | | Carboxyvinyl polymer | 0.2 |
| | | Xanthan gum | 0.1 |
| | E | Erythritol | 1.0 |
| | E | Mannitol | 0.5 |
| | | 1,3-Butanediol | 2.0 |
| | | Ginger extract | 0.1 |
| | | Yuzu extract | 0.1 |
| Total | | | 100 |
| ((A) + (B))/((A) + (B) + (C)) | | | 0.52 |
| (A)/((A) + (B)) | | | 0.17 |
| (E)/((A) + (B) + (C)) | | | 0.65 |
| X-ray structure analysis | | | α-type |
| Film formability | | | A |
| Permeation sensation | | | 8 |
| Lasting of moist skin | | | 9 |

*N-(Hexadecyloxyhydroxypropyl)-N-hydroxyethylhexadecanamide

Example 59

Semi-Transparent Gel

In a manner similar to that employed in Examples 1 to 10, an O/W emulsion composition (semi-transparent gel) having a formulation shown in Table 13 was produced. X-ray structural analysis of the composition was performed. The film formability and skin permeability of the composition, and lasting of moist skin attained by the composition were assessed. The results are also shown in Table 13.

TABLE 13

| | | (Ingredients) | (wt. %) |
|---|---|---|---|
| Phase I | D | Stearoylglutamic acid | 0.5 |
| | C | Pseudo-ceramide* | 2.0 |
| | C | CERAMIDE 2 | 0.1 |
| | B | Cetanol | 1.0 |
| | B | Stearyl alcohol | 0.5 |
| | A | Monostrearyl glyceryl ether | 0.5 |
| | A | Glyceryl monobehenate | 2.0 |
| | | Glycerin | 5.0 |
| Phase II | F | Water | bal. |
| | | Methylparaben | q.s. |
| | E | Xylitol | 0.7 |

TABLE 13-continued

| | (Ingredients) | (wt. %) |
|---|---|---|
| E | Threitol | 0.3 |
| | Carboxyvinyl polymer | 0.3 |
| | *Eucalyptus* extract | 0.1 |
| | *Thujopsis dolabrata* extract | 0.1 |
| | Altheae extract | 0.1 |
| | Seaweed extract | 0.1 |
| | L-Arginine | q.s. |
| Total | | 100 |
| ((A) + (B))/((A) + (B) + (C)) | | 0.66 |
| (A)/((A) + (B)) | | 0.63 |
| (E)/((A) + (B) + (C)) | | 0.16 |
| X-ray structure analysis | | α-type |
| Film formability | | A |
| Permeation sensation | | 9 |
| Lasting of moist skin | | 9 |

*N-(Hexadecyloxyhydroxypropyl)-N-hydroxyethylhexadecanamide

Example 60

Cream

In a manner similar to that employed in Examples 1 to 10, an O/W emulsion composition (cream) having a formulation shown in Table 14 was produced. X-ray structural analysis of the composition was performed. The film formability and skin permeability of the composition, and lasting of moist skin attained by the composition were assessed. The results are also shown in Table 14.

TABLE 14

| | | (Ingredients) | (wt. %) |
|---|---|---|---|
| Phase I | D | Sodium stearoylglutamate | 0.5 |
| | C | Pseudo-ceramide* | 3.5 |
| | C | CERAMIDE 3 | 0.5 |
| | B | Cetanol | 1.0 |
| | B | Cholesterol | 0.1 |
| | A | Glyceryl monobehenate | 1.5 |
| | A | Monostearoyl glyceryl ether | 0.5 |
| | | Stearic acid | 0.1 |
| | | Dimethylpolysiloxane | 5.0 |
| | | Olive oil | 5.0 |
| | | Squalane | 5.0 |
| | | Dicapryl carbonate | 0.5 |
| | | Petrolatum | 1.0 |
| | | Cholesteryl isostearate | 1.0 |
| | | Sorbitol | 2.0 |
| | | Glycerin | 15.0 |
| Phase II | F | Water | bal. |
| | D | Sodium methyl stearoyl taurate | 0.3 |
| | | Methylparaben | 0.3 |
| | | Phenoxyethanol | 0.2 |
| | | Xanthan gum | 0.2 |
| | | 1% Tuberosa polysaccharide | 2.0 |
| | E | Xylitol | 1.0 |
| Total | | | 100 |
| ((A) + (B))/((A) + (B) + (C)) | | | 0.44 |
| (A)/((A) + (B)) | | | 0.65 |
| (E)/((A) + (B) + (C)) | | | 0.14 |
| X-ray structure analysis | | | α-type |
| Film formability | | | A |
| Permeation sensation | | | 9 |
| Lasting of moist skin | | | 10 |

*N-(Hexadecyloxyhydroxypropyl)-N-hydroxyethylhexadecanamide

Example 61

Skin Lotion

Phase I ingredients were heated and mixed at 80 to 95° C. Under propeller-stirring (300 rpm), phase II ingredients, which had been heated to 80 to 95° C., were added to the phase I ingredients, to thereby form an emulsion. The emulsion was gradually cooled to 25° C., and phase III ingredients (25° C.) were added to the cooled emulsion, to thereby yield an O/W emulsion composition (skin lotion) having a formulation of Table 15. X-ray structural analysis of the composition was performed. The film formability and skin permeability of the composition, and lasting of moist skin attained by the composition were assessed. The results are also shown in Table 15.

TABLE 15

| | | (Ingredients) | (wt. %) |
|---|---|---|---|
| Phase I | A | Monostrearyl glyceryl ether | 0.25 |
| | B | Cetanol | 0.15 |
| | C | Pseudo-ceramide* | 0.6 |
| | D | 1-(2-Hydroxyethylamino)-3-isostearyloxy-2-propanol | 0.2 |
| | | Glycerin | 5.0 |
| Phase II | F | Water | bal. |
| | | L-Glutamic acid | 0.07 |
| | | Methylparaben | 0.2 |
| Phase III | | Water | 5.0 |
| | | Ethanol | 3.0 |
| | | 1,3-Butylene glycol | 3.0 |
| | E | Trehalose | 3.0 |
| | E | Raffinose | 2.0 |
| | | *Thujopsis dolabrata* extract | 0.5 |
| | | *Eucalyptus* extract | 0.5 |
| | | Amidinoproline | 0.2 |
| Total | | | 100 |
| ((A) + (B))/((A) + (B) + (C)) | | | 0.4 |
| (A)/((A) + (B)) | | | 0.63 |
| (E)/((A) + (B) + (C)) | | | 5.0 |
| X-ray structure analysis | | | α-type |
| Film formability | | | A |
| Permeation sensation | | | 8 |
| Lasting of moist skin | | | 9 |

*N-(Hexadecyloxyhydroxypropyl)-N-hydroxyethylhexadecanamide

Example 62

Essence Lotion

Phase I ingredients were heated and mixed at 80 to 95° C. Under propeller-stirring (300 rpm), phase II ingredients, which had been heated to 80 to 95° C., were added to the phase I ingredients, to thereby form an emulsion. The emulsion was gradually cooled to 25° C., and phase III ingredients (25° C.) were added to the cooled emulsion, to thereby yield an O/W emulsion composition (essence lotion) having a formulation of Table 16. X-ray structural analysis of the composition was performed. The film formability and skin permeability of the composition, and lasting of moist skin attained by the composition were assessed. The results are also shown in Table 16.

TABLE 16

| | | (Ingredients) | (wt. %) |
|---|---|---|---|
| Phase I | A | Monocetyl glyceryl ether | 0.7 |
| | B | Cetanol | 0.6 |
| | C | Pseudo-ceramide* | 2.0 |
| | D | Stearoylglutamic acid | 0.2 |
| | E | Lactose | 2.0 |
| | E | Sucralose | 2.0 |
| Phase II | F | Water | bal. |
| | | L-Arginine | 0.14 |
| | | Methylparaben | 0.2 |
| Phase III | | Dimethylpolysiloxane | 3.0 |
| | | Carboxyvinyl polymer | 0.1 |
| | F | Water | 15.0 |
| | | Tuberosa polysaccharide liq. | 5.0 |
| | | Dipropylene glycol | 5.0 |
| | | Horse chestnut extract | 0.2 |
| | | Chamomile extract | 0.2 |
| | | Yuzu extract | 0.2 |
| | | Clove extract | 0.2 |
| | | Altheae extract | 0.2 |
| | | Tea extract | 0.2 |
| | | Lemon extract | 0.2 |
| | | Seaweed extract | 0.1 |
| Total | | | 100 |
| ((A) + (B))/((A) + (B) + (C)) | | | 0.39 |
| (A)/((A) + (B)) | | | 0.54 |
| (E)/((A) + (B) + (C)) | | | 1.21 |
| X-ray structure analysis | | | α-type |
| Film formability | | | A |
| Permeation sensation | | | 9 |
| Lasting of moist skin | | | 9 |

*N-(Hexadecyloxyhydroxypropyl)-N-hydroxyethylhexadecanamide

Example 63

Milky Lotion

In a manner similar to that employed in Examples 1 to 10, an O/W emulsion composition (milky lotion) having a formulation shown in Table 17 was produced. X-ray structural analysis of the composition was performed. The film formability and skin permeability of the composition, and lasting of moist skin attained by the composition were assessed. The results are also shown in Table 17.

TABLE 17

| | | (Ingredients) | (wt. %) |
|---|---|---|---|
| Phase I | A | Sorbitan monostearate | 0.6 |
| | B | Cetanol | 0.6 |
| | B | Stearyl alcohol | 0.4 |
| | C | Pseudo-ceramide* | 2.0 |
| | D | Polyoxyethylene(40) hydrogenated castor oil | 1.0 |
| | D | Sodium methyl stearoyl taurate | 0.3 |
| | D | Polyoxyethylene(20) sorbitan monostearate (HLB 14.9) | 1.4 |
| | | Squalane | 3.0 |
| | | Pentaerythritol tetraoctanoate | 3.0 |
| | | Glyceryl tri(2-ethylhexanoate) | 3.0 |
| | | Cetyl octanoate | 1.0 |
| | | Glycerin | 3.0 |
| | E | Galactosylfructose | 2.5 |
| | E | Melibiose | 2.5 |
| Phase II | | Dimethylpolysiloxane | 3.0 |
| | | Carboxyvinyl polymer | 0.2 |
| Phase II (cont.) | F | Water | bal. |
| | | Phenoxyethanol | 0.3 |
| | | Methylparaben | 0.1 |
| | | Potassium hydroxide | q.s. |
| Total | | | 100 |
| ((A) + (B))/((A) + (B) + (C)) | | | 0.44 |
| (A)/((A) + (B)) | | | 0.38 |
| (E)/((A) + (B) + (C)) | | | 1.39 |
| X-ray structure analysis | | | α-type |
| Film formability | | | A |
| Permeation sensation | | | 9 |
| Lasting of moist skin | | | 9 |

*N-(Hexadecyloxyhydroxypropyl)-N-hydroxyethylhexadecanamide

Example 64

Cream

In a manner similar to that employed in Examples 1 to 10, an O/W emulsion composition (cream) having a formulation shown in Table 18 was produced. X-ray structural analysis of the composition was performed. The film formability and skin permeability of the composition, and lasting of moist skin attained by the composition were assessed. The results are also shown in Table 18.

TABLE 18

| | | (Ingredients) | (wt. %) |
|---|---|---|---|
| Phase I | A | Glyceryl monobehenate | 1.25 |
| | B | Cetanol | 0.8 |
| | B | Stearyl alcohol | 1.2 |
| | C | Pseudo-ceramide*1 | 4.0 |
| | D | 1-(2-Hydroxyethylamino)-3-isostearyloxy-2-propanol | 0.2 |
| | | Hydrogenated lecithin | 0.05 |
| | B | Cholesterol | 0.75 |
| | | Petrolatum | 1.75 |
| | | Dimethylpolysiloxane | 3.0 |
| | | BRS661-C*2 | 0.5 |
| | | Glycerin | 15.0 |
| Phase II | F | Water | bal. |
| | | L-Glutamic acid | 0.18 |
| | | Methylparaben | 0.2 |
| | | Polyethylene glycol | 2.0 |
| | E | Trehalose | 5.0 |
| Total | | | 100 |
| ((A) + (B))/((A) + (B) + (C)) | | | 0.49 |
| (A)/((A) + (B)) | | | 0.38 |
| (E)/((A) + (B) + (C)) | | | 0.69 |
| X-ray structure analysis | | | α-type |
| Film formability | | | A |
| Permeation sensation | | | 9 |
| Lasting of moist skin | | | 10 |

*1 N-(hexadecyloxyhydroxypropyl)-N-hydroxyethylhexadecanamide
*2 Bismethoxypropylamideisodocosane

The invention claimed is:

1. An emulsion composition comprising the following ingredients (A), (B), (C), (D), (E), and (F):

(A) from 0.05 to 7 wt. % of at least one compound selected from the group consisting of glyceryl monobehenate and monocetyl glyceryl ether;

(B) from 0.05 to 7 wt. % of cetanol;
(C) from 0.05 to 7 wt. % of at least one compound of the following formula (2):

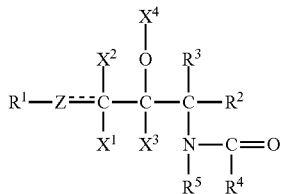

wherein
- $R^1$ represents a C4 to C30 linear, branched, or cyclic, saturated or unsaturated hydrocarbon group which may be substituted by a hydroxyl group, a carbonyl group, or an amino group;
- Z represents a methylene group, a methine group, or an oxygen atom;
- each of $X^1$, $X^2$, and $X^3$ represents a hydrogen atom, a hydroxyl group, or an acetoxy group;
- $X^4$ represents a hydrogen atom, an acetyl group, or a glyceryl group, or forms an oxo group together with the adjacent oxygen atom, wherein when Z is a methine group, one of $X^1$ and $X^2$ is a hydrogen atom, and the other is absent, and when $X^4$ forms an oxo group, $X^3$ is absent;
- each of $R^2$ and $R^3$ represents a hydrogen atom, a hydroxyl group, a hydroxymethyl group, or an acetoxymethyl group;
- $R^4$ represents a C5 to C60 linear, branched, or cyclic, saturated or unsaturated hydrocarbon group which may be substituted by a hydroxyl group, a carbonyl group, or an amino group and which may have an ether bond, an ester bond, or an amide bond in a backbone thereof; and
- $R^5$ represents a hydrogen atom, or a linear or branched, saturated or unsaturated hydrocarbon group optionally having a substituent selected from the group consisting of a hydroxyl group, a hydroxyalkoxy group, an alkoxy group, and an acetoxy group and containing 1 to 30 carbon atoms in total; and the broken line represents an optional unsaturated bond;

(D) from 0.01 to 7 wt. % of at least one compound selected form the group consisting of a stearoylglutamic acid salt and a sphingosine salt;
(E) from 0.01 to 5 wt. % of xylitol; and
(F) water,
wherein a weight ratio (E)/(A)+(B)+(C) is from 0.01 to 3.

2. The emulsion composition according to claim 1, wherein the weight ratio of the ingredients (A), (B), and (C), ((A)+(B))/((A)+(B)+(C)), is from 0.15 to 0.95.

3. The emulsion composition according to claim 1, wherein the weight ratio of the ingredients (A) and (B), (A)/((A)+(B)), is from 0.25 to 0.75.

4. The emulsion composition according to claim 1, wherein a weight ratio of the ingredients (A), (B), (C), and (D), (D)/((A)+(B)+(C)), is form 0.04 to 1.

5. A method for producing an emulsion composition according to claim 1, the method comprising mixing the ingredients (A) to (E) with an aqueous phase containing ingredient (F), thereby forming the emulsion.

6. A method for producing an emulsion composition according to claim 1, the method comprising mixing the ingredients (A) to (D) with an aqueous phase containing ingredients (E) and (F), thereby forming the emulsion.

* * * * *